United States Patent [19]

Degen et al.

[11] Patent Number: 5,685,991

[45] Date of Patent: *Nov. 11, 1997

[54] INTEGRITY-TESTABLE WET-DRY-REVERSIBLE ULTRAFILTRATION MEMBRANES AND METHOD FOR TESTING SAME

[75] Inventors: Peter J. Degen, Huntington; John Mischenko, III, Amityville, both of N.Y.; Robert E. Kesting, Sumner, Wash.; Moira H. Bilich, Massapequa; Trevor A. Staff, Bronx, both of N.Y.

[73] Assignee: Pall Corporation, East Hills, N.Y.

[*] Notice: The term of this patent shall not extend beyond the expiration date of Pat. No. 5,480,554.

[21] Appl. No.: 542,293

[22] Filed: Oct. 12, 1995

Related U.S. Application Data

[63] Continuation of Ser. No. 882,473, May 13, 1992, Pat. No. 5,480,554.

[51] Int. Cl.$^6$ .................................................. B01D 61/00
[52] U.S. Cl. .................... 210/651; 210/500.41; 210/645; 264/41
[58] Field of Search .......................... 210/651, 500.41, 210/634, 637, 639, 645; 264/41

[56] References Cited

U.S. PATENT DOCUMENTS

| | | |
|---|---|---|
| 3,615,024 | 10/1971 | Michaels . |
| 3,691,068 | 9/1972 | Cross . |
| 3,931,123 | 1/1976 | Vacik et al. . |

(List continued on next page.)

FOREIGN PATENT DOCUMENTS

| | | |
|---|---|---|
| 0 037 185 | 10/1981 | European Pat. Off. . |
| 0 139 202 | 5/1985 | European Pat. Off. . |
| 0 202 849 | 11/1986 | European Pat. Off. . |
| 0 396 258 | 11/1990 | European Pat. Off. . |
| 2 314 215 | 1/1977 | France . |
| 224665 | 7/1985 | Germany . |
| 2 020 300 | 11/1979 | United Kingdom . |
| 2 047 162 | 11/1980 | United Kingdom . |
| 2 266 851 | 11/1993 | United Kingdom . |

OTHER PUBLICATIONS

Patent Abstracts of Japan, vol. 12, No. 198 (C-502), JP 63001406A, Jan. 6, 1988.
Patent Abstracts of Japan, vol. 12, No. 47 (C-475), JP 62193604A, Aug. 25, 1987.
Anderson et al., *Science*, 252, 1412-1414 (1991).
Capannelli et al., *Characterization of Porous Solids*, Unger et al., eds., Elsevier Science Publishers B.V., Amsterdam, 283-293 (1988).

(List continued on next page.)

*Primary Examiner*—Ana Fortuna
*Attorney, Agent, or Firm*—Leydig, Voit & Mayer, Ltd.

[57] ABSTRACT

The present invention provides for the first time ultrafiltration/diafiltration membranes that are capable of excluding 0.02 μm diameter, monodisperse, latex particles and are capable of being dried without loss of such ultrafiltration properties. A rapid, reliable method for integrity testing membranes also has now been discovered. The test has particular applicability to ultrafiltration membranes, although it may also be used for testing microfiltration membranes as well. In accordance with the method, referred to as the $K_{UF}$ method, the membrane to be tested is first thoroughly wetted with a wetting liquid that is capable of fully wetting the membrane; a displacing liquid is placed in contact with one side of the wetted membrane and increasing pressure is then applied to said displacing liquid; and the flow rate through said membrane is measured as a function of the applied pressure; wherein the displacing liquid is substantially insoluble in the wetting liquid and the interfacial tension between the two liquids is about 10.0 dynes/cm or less. A plot of the flow rate of liquid, per unit area of the membrane, through the membrane as a function of applied pressure can be made and a straight line may be drawn through the steep part of the resulting curve, using regression analysis, which will intersect the horizontal axis at a given pressure value, which is then the $K_{UF}$ value.

34 Claims, 14 Drawing Sheets

U.S. PATENT DOCUMENTS

| | | |
|---|---|---|
| 3,939,049 | 2/1976 | Ratner et al. . |
| 3,945,900 | 3/1976 | Klinkowski . |
| 3,977,967 | 8/1976 | Trulson et al. . |
| 3,994,860 | 11/1976 | Brousse . |
| 4,026,977 | 5/1977 | Bourganel . |
| 4,033,822 | 7/1977 | Gregor . |
| 4,060,488 | 11/1977 | Hoover et al. . |
| 4,134,837 | 1/1979 | Yamashita et al. . |
| 4,177,150 | 12/1979 | Inoue et al. . |
| 4,203,847 | 5/1980 | Grandine, 2nd . |
| 4,207,182 | 6/1980 | Marze . |
| 4,208,508 | 6/1980 | Hashino et al. . |
| 4,320,009 | 3/1982 | Hilton et al. . |
| 4,340,479 | 7/1982 | Pall . |
| 4,358,378 | 11/1982 | Iwama et al. . |
| 4,431,545 | 2/1984 | Pall et al. ................... 210/641 |
| 4,439,322 | 3/1984 | Sonoda et al. . |
| 4,451,424 | 5/1984 | Tweedle et al. . |
| 4,473,474 | 9/1984 | Ostreicher et al. . |
| 4,481,260 | 11/1984 | Nohmi . |
| 4,618,533 | 10/1986 | Steuck . |
| 4,672,113 | 6/1987 | Wallisch et al. . |
| 4,810,384 | 3/1989 | Fabre . |
| 4,814,082 | 3/1989 | Wrasidlo . |
| 4,816,252 | 3/1989 | Stott et al. . |
| 4,822,489 | 4/1989 | Nohmi et al. . |
| 4,857,201 | 8/1989 | Black et al. . |
| 4,871,494 | 10/1989 | Kesting et al. . |
| 4,880,441 | 11/1989 | Kesting et al. . |
| 4,902,422 | 2/1990 | Pinnau et al. . |
| 4,902,424 | 2/1990 | Wrasidlo . |
| 4,906,375 | 3/1990 | Heilmann . |
| 4,908,267 | 3/1990 | Kohn . |
| 4,954,381 | 9/1990 | Cabasso et al. . |
| 4,968,733 | 11/1990 | Müller et al. . |
| 4,976,859 | 12/1990 | Wechs . |
| 4,990,252 | 2/1991 | Tomaschke et al. . |
| 4,992,221 | 2/1991 | Malon et al. . |
| 4,992,485 | 2/1991 | Koo et al. . |
| 4,997,565 | 3/1991 | Niesen . |
| 5,017,292 | 5/1991 | DiLeo et al. . |
| 5,022,990 | 6/1991 | Doi et al. . |
| 5,069,945 | 12/1991 | Wrasidlo . |
| 5,076,935 | 12/1991 | Kraus et al. . |
| 5,468,390 | 11/1995 | Crivello et al. . |
| 5,480,554 | 1/1996 | Degen et al. ................... 210/651 |

OTHER PUBLICATIONS

Capannelli et al., *Journal of Membrane Science*, 15, 289–313 (1983).
Chen et al., *J. Membrane Sci.*, 48, 203–19 (1990).
Database WPI, Derwent Publications Ltd., 83–28523K/12 (JP58024305 abstract) (Feb. 14, 1983).
Database WPI, Derwent Publications Ltd., 83–773589/39 (JP58139702 abstract) (Aug. 19, 1983).
Database WPI, Derwent Publications Ltd., 84–099899 (SU1028687 abstract) (Jul. 15, 1983).
Database WPI, Derwent Publications Ltd., 86–167043/26 (JP61101204 abstract) (May 20, 1986).
Database WPI, Derwent Publications Ltd., 89–181842/25 (JP1119308 abstract) (May 11, 1989).
Database WPI, Derwent Publications Ltd., 89–215629/30 (JP1151922 abstract) (Jun. 14, 1989).
Database WPI, Derwent Publications Ltd., 90–048948/07 (JP2002862 abstract) (Jan. 8, 1990).
Database WPI, Derwent Publications Ltd., 90–069979/10 (JP2021560 abstract) (Jan. 24, 1990).
DiLeo et al., *Nature*, 351, 420–421 (1991).
Doi et al., *Desalination*, 80, 167–180 (1991).
Erbe, *Kolloindnyj Zurnel*, 277–285 (1933).
Hampl et al., *Collection Czechoslov. Chem. Commun.*, 32, 4181–4189 (1967).
Kleper, *BioPharm*, 13, (Nov./Dec. 1990).
Lafrenier et al., *Ind. Eng. Chem. Prod. Res.*, 26(11), 2385 (1987).
Merrill et al., *ASAIO J.*, 6, 60–64 (1983).
Miyano et al., *J. Appl. Polym. Sci.*, 41, 407–417 (1990).
Passlack et al., *Die Angewandte Makromolekulare Chemie*, 139(2280), 175–189 (1986).
Philips Abstract on "Novel Liquid–Porosmetric Integrity for Correlating Virus Retention" (date unknown).
Ray et al., *J. Membrane Sci.*, 23, 155–182 (1985).
Technical Bulletin, "Ultrafiltration and Microfiltration—Hollow Fiber Membranes", A/G Technology Corporation (date unknown).
Tsay et al., *J. Polym. Sci.*, Part B, 1327–1365 (1990).
Tweedle et al., *Ind. Eng. Chem. Prod. Res. Dev.*, 22, 320–326 (1983).

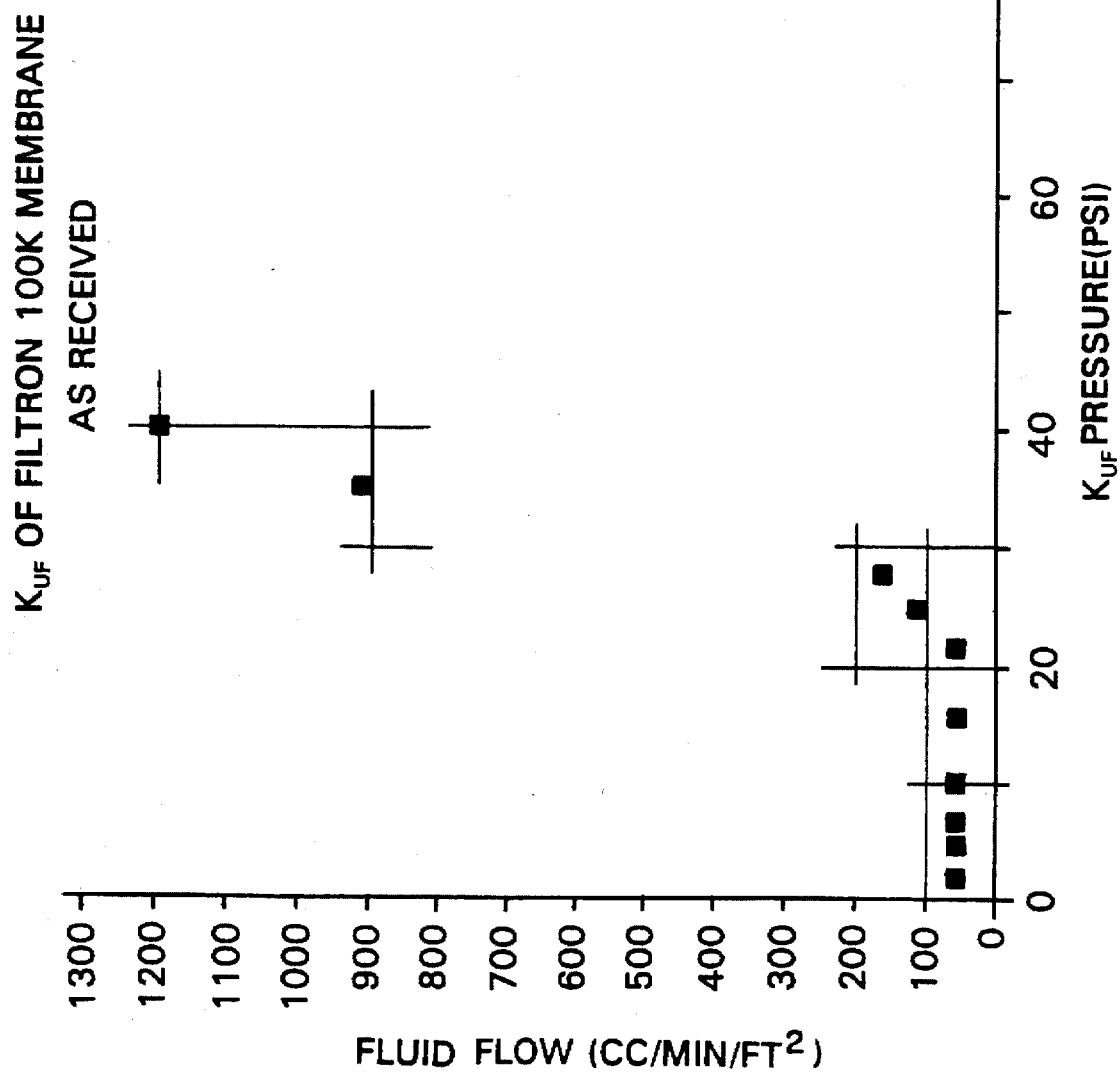

5,685,991

INTEGRITY-TESTABLE WET-DRY-REVERSIBLE ULTRAFILTRATION MEMBRANES AND METHOD FOR TESTING SAME

This is a continuation of application Ser. No. 07/882,473 filed on May 13, 1992, now U.S. Pat. No. 5,480,554.

FIELD OF THE INVENTION

This invention relates to the field of filtration membranes, generally, and specifically to the field of ultraporous membranes, particularly ultrafiltration and diafiltration membranes.

BACKGROUND OF THE INVENTION

Ultrafiltration (UF) and diafiltration (DF) are pressure-driven membrane separation processes which are used to separate (by a sieving mechanism) macromolecules such as proteins from solutions containing solvents and low MW solutes. Ultrafiltration and diafiltration processes are similar and identical membranes are used for both. In UF, no additional solvent (water) is added to the solution which is being filtered while filtration is in progress; in DF additional solvent is added during filtration. If a solution contains macromolecules of sufficiently great size differences, then (UF) or (DF) can also be used to fractionate these macromolecules.

The filtration regime which comprises UF or DF lies on the spectrum of pressure driven membrane separation processes between hyperfiltration (HF), also known as reverse osmosis, on its fine-pored side and microfiltration (MF) on its coarse-pored side. The UF regime covers the pore diameter range between 0.001 and 0.02 μm (10–200 Å). Ultrafiltration is also described in terms of the molecular weigh cutoff (MWCO) capabilities of its membranes. It consists of membranes with MWCO between about 500 and several million.

Asymmetric, integrally-skinned UF membranes are prepared by a generalized process known as phase inversion in which a multicomponent polymer solution (sol) consisting (usually) of three components: polymer, solvent, and pore-former (nonsolvent, swelling agent, or weak solvent) is induced to separate into two interdispersed liquid phases prior to coagulation into a solid membrane gel. To effect the separation into two interdispersed liquid phases, polymer miscibility in the solvent vehicle is lowered by one of these techniques:

1.) Solvent evaporation (Dry Process);
2.) Exchange of solvent for nonsolvent (Wet Process); and
3.) Lowering solution temperature (thermal process).

Two general structural varieties of asymmetric, integrally-skinned, phase inversion UF membranes are known in the art. Representative of the first is U.S. Pat. No. 3,615,024, which is the original and still most commonly encountered variety of ultrafiltration membrane, consisting essentially of a bilayer having a thin skin exhibiting what has been termed slit-like fissures or cracks, and a thick substructure containing a high concentration of finger-like intrusions or macrovoids. The macrovoids often extend from one surface to the other although they are sometimes buried more deeply within the matrix. Ideally, an integral skin covers the macrovoids but, in practice, some of the skin above the macrovoids is cracked, thereby breaking the integrity of the skin and enabling the passage of large particles. These membranes are supplied wetted with a pore supporting fluid since they cannot tolerate full dryness without severe loss of filtration performance. Bacteriostats, which must be washed out of the membrane before usage, are often present in membranes that are supplied wet. Some manufacturers indicate in their catalogs that a membrane is being supplied "dry", however these membranes may contain humectants such as glycerol as a pore supporting fluid. As with bacteriostats, humectants must be removed from the membrane by soaking, flushing or by some other method that never permits the membrane to become fully dried.

Representative of the second general type of ultrafiltration membrane is that obtained in accordance with U.S. Pat. Nos. 4,954,381 and 4,451,424, which purportedly produce integrally-skinned UF membranes with macrovoid-free matrices by increasing the viscosity of the casting solution through the addition of water soluble viscosity enhancing polymeric additives such as polyvinylpyrrolidone (PVP) or polyethyleneglycol (PEG). These membranes exhibit a skin with a pore size distribution which is too broad to be integrity-tested because of the leaching out of the polymeric additives during precipitation and washing steps, as well as during their use in the UF process. These membranes can be supplied "dry" (i.e. no free liquid present), but contain high concentrations of residual PVP or PEG. Humectants such as glycerol, PVP, PEG and/or water and other wetting fluids may act as plasticizers to diminish friability. These materials may also act as pore supporting fluids which if removed lead to cracks and other defects in the membrane skin.

Additionally, the pore size increases with the molecular weight (MW) of the extractable additive, which is in turn related to the breadth of the pore size distribution of these membranes.

Although widely used, ultrafiltration membranes are recognized to suffer from some serious drawbacks. For example, nearly all ultrafiltration/diafiltration membranes contain a humectant such as glycerol or must be maintained in a wetted state at all times, including during shipping, because the filtration properties of the membrane are unstable owing to the presence of defects. Once the humectant or other supporting liquid is removed and the membrane is dried and rewetted, the performance is altered and the membrane skin becomes cracked and the membrane useless. This means that as a practical issue, all ultrafiltration/diafiltration membranes must be shipped along with a large amount of wetting liquid, usually water, increasing shipping costs. Further, the requirement that the membrane be maintained in a wetted state also is a substantial burden on the users who must assure that the membrane is never allowed to dry. The fact that the membranes are constantly maintained in a wetted state also means that the risk of bacterial growth is present. requiring then that a bacteriostat, or the like, be present in the wetted membrane. Unfortunately, the, presence of a bacteriostat also introduces the problem of contamination of the product stream by the membrane, for once such an agent is present, it is difficult, if not impossible to remove.

In the case of membranes containing a humectant such as glycerol, the membrane must be soaked in several changes of water or other solvent in order to remove as much of the foreign material as possible. Then once the pore structure is supported with the solvent the sample must never be permitted to dry out.

Another significant problem with all currently available ultrafiltration/diafiltration membranes is the presence of significant defects in the membrane. Such defects include macrovoids, cracks, pinholes, and other defects and imperfections that either breach the skin layer or lead to failure of the membrane. The presence of such defects means, however, that although a given membrane may be rated with a removal rating that would indicate, for example, that the membrane is capable of removing materials of moderate molecular weight (between 1,000 to 500,000) from liquid, the presence of the defects allows a given portion of the substances to pass through the membrane, which, of course, is very undesirable. Even relatively large particles such as latex spheres are known to pass through UF membrane defects.

Molecular weight cutoff is an expression of the retention characteristics of a membrane in terms of molecules of known sizes. Retention is commonly rated as that molecular weight cutoff at which at least 90 percent of spherical uncharged molecules of that same molecular weight will be retained by the porous membrane, whereas less than about 50 percent of such molecules of significantly lower molecular weight will be retained. However, linear molecules with molecular weights greater than the molecular weight cutoff may pass through the membrane because the effective diameter of a linear molecule is smaller than that of a spherical molecule. Linear molecules may approach a membrane pore "end on" and thread themselves through the pore. This can occur if a long chain linear molecule is aligned with the laminar flow lines of the fluid passing through the membrane. On the other hand, charged molecules less than the molecular weight cutoff may not pass through the membrane due to electrostatic interactions with the membrane. In ultrafiltration membranes, the molecular weight cutoff ranges from about 500 or 1000 up to about several million corresponding to pore sizes of 10 to 200 Å.

Although a limited number of ultrafiltration membranes have been recently introduced in the form of hollow fibers, with indicated nominal molecular weight cutoff ratings in the 1,000 to several million range, which membranes are capable of being shipped in the dry state, such membranes still suffer from the very significant problem of having defects in their structure, rendering them of only limited value.

Because of the wide and large number of applications for ultrafiltration membranes, considerable effort has been spent to improve the effectiveness of such membranes, but to date, with limited success. Many patents and articles have been published regarding the manufacture of ultrafiltration membranes, some claiming them to be "defect-free", and some claiming them to be dryable, but the fact remains that no ultrafiltration membrane has heretofore been produced that is both dryable and which is free of defects.

Present-day ultrafiltration membranes work on a statistical basis, i.e. as only a small portion of liquid being filtered passes through defects in the membrane, and as only a portion of all liquid being filtered contains the material to be removed, the probability is that only a small amount of the material to be removed will pass through the membrane. If, however, the material being filtered is, for example, a pharmaceutical composition and the material to be removed is a bacterium, and bacteria does pass through the membrane, the patient who becomes ill by using the contaminated product will not care very much about probabilities.

Again, the problem with ultrafiltration membranes made in accordance with any of the prior art processes is that they are not capable of being dried without a humectant supporting the pore structure and/or they are not free of the various defects described earlier, rendering them of only limited value.

Further, as with many processes for manufacturing membranes, absolute predictability of the performance and the quality of the finished product is not possible, hence a method of testing the integrity of the finished membrane product is needed. Unfortunately, there presently is no useful way to test the integrity of an ultrafiltration membrane, and certainly no rapid way to do so. With respect to microfiltration membranes and other types of porous filter media, the tests known as the "bubble point" (ASTM F316-86) and time $K_L$ U.S. Pat. No. 4,340,479) methods have been employed for many years to characterize the porosity of such structures. However, due to the extremely small pore sizes encountered in ultrafiltration membranes neither the $K_L$ nor the "bubble point" test can be applied successfully. As the pore size of a membrane decreases, the pressure required to carry out a "bubble point" or $K_L$ test increases. On an ultrafiltration membrane such test pressures would crush or otherwise damage the membrane.

In the case of ultrafiltration membranes generally, there is considerable difficulty in directly observing and measuring pores and pore sizes, as by scanning electron microscopy, for example. It has become common in the art to employ molecular weight cutoff values as discussed above, as an inferential and indirect technique for the determination of pore sizes. As a general proposition, the functional diameter of pores is approximately equal to the cube root of time molecular weight of the largest generally spherical, globular molecule, free of electric charge, which can pass through the membrane, while by convention the size of the smallest such molecule which is retained to the required extent of 90 percent represents the molecular weight cutoff. These determinations are well known to those of ordinary skill in the art. Clearly, however, such a test provides only approximations of the true porosity of any given ultrafiltration structure and, further, is not a test that may be rapidly employed. The measurement of molecular weight cutoffs is also fraught with complications such as the adsorption of the test substance on the membrane surfaces accompanied by the plugging of the sample during the test. A typical molecular weight cutoff test could require hours or even days to complete. Instead of characterizing membranes in terms of some standard test parameter such as $K_L$ or pore size, broad ranges of molecular weight cutoff are generally cited in product catalogs and in the technical literature.

Because a reliable, rapid test for evaluating the integrity, molecular weight cutoff and pore size rating of ultrafiltration membranes is an absolute necessity for the reliable, consistent production of UF/DF membranes, a great need exists for such a test.

SUMMARY OF THE INVENTION

The present invention provides for the first time ultrafiltration membranes that are capable of being dried without loss of such ultrafiltration properties. Such membranes may be selectively manufactured to have any particular molecular weight cutoff ratings, from about 1,000 daltons to about 500,000 daltons. In addition membranes with a rated molecular weight cutoff of $\leq 20,000$ are capable of excluding 0.02 µm diameter, monodisperse, latex particles to rejection coefficients of >0.998. Membranes with rated molecular cutoffs of $\leq 100,000$ are capable of excluding 40 nanometer diameter, monodisperse, latex particles to rejection coefficients of >0.998. Membranes with rated molecular cutoffs of $\leq 500,000$ are capable of excluding 0.1 µm diameter, monodisperse, latex particles to rejection coefficients of >0.998.

The membranes of the present invention will generally have a pore size from about 200 Å down to about 10 Å. Membranes of particular interest may be comprised of polyethersulfone, polysulfone or polyarylsulfone modified or unmodified.

There is also provided a process for filtering a fluid comprising causing said fluid to flow through such a filtration membrane. Such a process may include the filtration of fluids to remove proteins, for example, when the membrane has a molecular weight cutoff of from about 1,000 to about 30,000 daltons. Filtration of fluids to selectively remove proteins or viruses, such as from blood and blood serum, is also possible, as when the membrane has a molecular weight cutoff of about 500,000 daltons.

A new, rapid, reliable method for determining the molecular weight cutoff and pore size rating of UF/DF membranes has also now been discovered. The test has particular applicability to ultrafiltration and/or diafiltration membranes, although it may also be used for testing microfiltration membranes. In accordance with the method, referred to as the $K_{UF}$ method, the membrane to be tested is first thoroughly wetted with a wetting liquid that is capable of fully wetting the membrane; a displacing liquid, which is immiscible with the liquid used to wet the membrane, is placed in contact with the upstream side of the wetted membrane. Pressure is then applied to said displacing liquid and said pressure increased beyond the point where the displacing liquid begins to flow through the membrane; and the flow rate of liquid that passes through said membrane is measured as a function of the applied pressure; wherein the displacing liquid is substantially insoluble in the wetting liquid and the interfacial tension between the two liquids is about 10.0 dynes/cm or less. Controlling the interfacial tension to less than 10 dynes/cm allows fluid displacement to be achieved at much lower pressures than similar testing normally performed with a water/air interface (i.e. $K_L$ or bubble point measurement). In addition it is important that the interfacial tension between the two liquids remain constant during the test procedure. A plot of the flow rate of displacing liquid, per unit area of the membrane, through the membrane as a function of applied pressure can be made and a straight line may be drawn through the steep part of the resulting curve, using regression analysis, which will intersect the horizontal axis at a given pressure value, which is then deemed the $K_{UF}$ value. FIG. 12 is an illustration of an idealized $K_{UF}$ curve in which the $K_{UF}$ value or characteristic pressure has been determined. The solid line represents the curve obtained by plotting flow rate vs pressure and the dotted line represents the extrapolation of the steep part of the curve to the pressure axis. The $K_{UF}$ value or characteristic pressure is a read from the graph at the point where the dotted line crosses the pressure axis and is a measure of the molecular weight cutoff of the membrane.

The membranes of the present invention may be characterized as having a $K_{UF}$ value of from about 5 psi to about 120 psi, preferably from about 10 psi to about 120 psi., determined using 1-butanol, saturated with water, as the wetting liquid, and water, saturated with 1-butanol, as the displacing liquid. The immiscible phases are mutually saturated to ensure that the interfacial tension between the liquids does not change due to dissolution of one phase into the other. Other factors such as temperature should also remain relatively constant during the test procedure so as to avoid substantial changes in the interfacial tension between the immiscible liquids.

A process for manufacturing an ultrafiltration membrane is provided. The method comprises dissolving a polymeric resin in a carrier comprising both a solvent for the resin and a nonsolvent for the resin, wherein the resin is present in an amount from about 15 to about 20 weight percent, and the amount of nonsolvent is from about 26 to about 34 percent of the solution, rapidly mixing the solution under high shear conditions to reduce or eliminate the presence of gel particles, filtering the solution to remove any gel particles that are present, degassing the solution to remove any entrained gas, casting or spinning the solution onto a support, and contacting the resulting cast or spun solution with a setting bath that comprises both a solvent and a nonsolvent for the resin, the ratio of solvent to nonsolvent being from about 1.5:1 to about 2:1.

A general method for manufacturing any ultrafiltration or membranous structure is also provided wherein an initial solution comprising a polymeric solute, a solvent therefor, and optionally a nonsolvent, is cast or extruded under a first set of process conditions, optionally onto or into a setting bath, containing a nonsolvent for the polymer, and optionally a solvent therefor, to form a desired membrane, thoroughly wetting a portion of the membrane to be tested with an initial wetting liquid that is capable of fully wetting the membrane, placing a displacing liquid that is immiscible with the wetting liquid in contact with the upstream side of the wetted membrane, applying increasing pressure to said displacing liquid and measuring the flow of displacing liquid that passes through said membrane as a function of the applied pressure, wherein the displacing liquid is substantially insoluble in the wetting liquid and the interfacial tension between the wetting liquid and the displacing liquid is about 10.0 dynes/cm or less, and adjusting one or more of the following process variables:

(1) the composition of the initial solution,
(2) the composition of the setting bath, and
(3) the rate at which the casting resin is mixed,
(4) the casting solution temperature, or the spinning temperature, in response to said measurement.

BRIEF DESCRIPTION OF THE DRAWINGS

FIGS. 11A and 11B are $K_{UF}$ graphs for a commercially available UF membrane comparing the $K_{UF}$ curve shapes before (FIG. 11A) and after (FIG. 11B) 1 wet/dry cycle.

Figure 1:
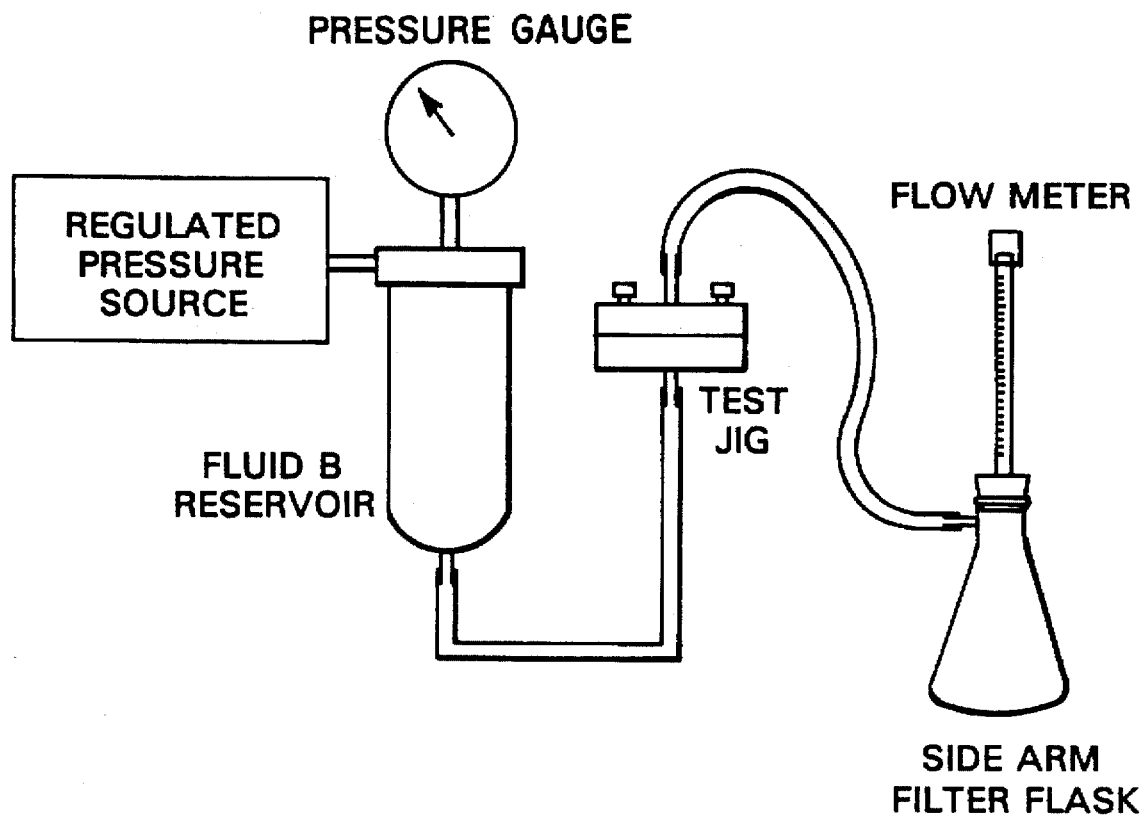
FIG. 1 is a diagram of an apparatus for measuring $K_{UF}$ in accordance with the present invention.

DETAILED DESCRIPTION OF THE PREFERRED EMBODIMENTS THE MEMBRANES AND METHOD OF MANUFACTURE POLYMERS

By following the principles of the present invention, it is possible to make ultrafiltration/diafiltration membranes possessing the aforedescribed properties, including the freedom from major defects, which breach the skin of the membrane. Various polymer types, such as polyethersulfone, polysulfone, polyphenylsulfone and the like may be employed in accordance with the present invention. For sake of brevity, the invention will be described in terms of the aromatic polysulfones and polyethersulfones, particularly the latter, with the understanding that the invention described in the application has broader application to other membrane structures.

The aromatic polysulfone type resin to be used for forming the membrane includes aromatic polysulfones and aromatic polyethersulfones, respectively, comprised of recurring units of the general formulae (I), (II) & (III).

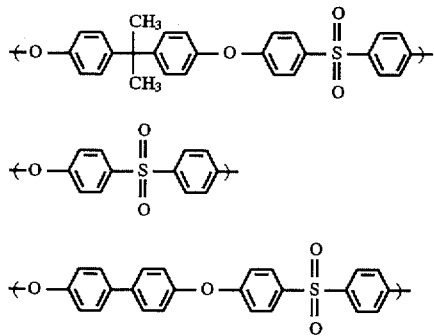

Several common proprietary commercial grades of polyarylether polymers useful by the present invention are illustrated by the following formulae:

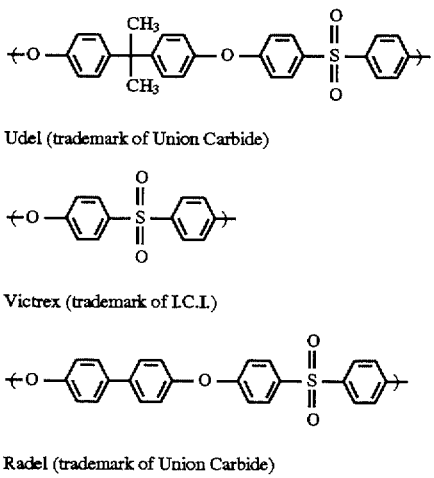

Other suitable polyethersulfones and their preparation are disclosed in "Synthesis of Poly(arylene sulphones) by Polycondensation of Arylsulphonyl Chlorides under Friedel-Crafts Conditions" by Cudby, et.al., Polymer,6,589 (1965), "Structures of the Poly(diphenylene ether sulphones) Obtained by Polysulphonylation," by Cudby et. al., Polymer, 9,265 (1965), British Pat. No. 1,016,245 and U.S. Pat. Nos. 4,008,203, 4,105,636 and 4,108,837, all of which are incorporated herein by reference.

These aromatic polysulfone, polyethersulfone, and polyphenylsulfone type resins each preferably have a number average molecular weight of 20,000 to 100,000, and most preferably from about 30,000 to about 50,000.

CASTING SOLUTIONS

The solvent system (vehicle) for the resin, such as polyethersulfone, comprises at least one solvent and at least one nonsolvent. Examples of suitable solvents include DMF, DMAC, DMSO, NMP, and formylpiperidine (FP). Preferred non-solvents are propionic acid, butyric acid, and isobutyric acid.

The preferred casting or spinning solution will comprise from about 15 to about 20 percent resin, such as polyethersulfone, more preferably from about 16 to about 19, and most preferably about 17 or 18. Further the ratio of solvent to nonsolvent is preferably from about 1.5 to about 2, most preferably from about 1.5 to about 1.9, and usually about 1.7.

Further, it is very important that the casting solution be free of contaminant particles, such as gel particles, and is substantially free of dissolved gases. Thus, the solution should be mixed extremely well, as with a high shear mixer, filtered, and degassed prior to casting membranes. The degassing is important in that if the solution is not properly degassed, the result will be a membrane with substantial defects, such as pinholes.

MEMBRANE GELATION BATHS

A gelation bath is used which consists of a non-solvent medium containing nonsolvent and an appreciable amount of solvent. Pore size increases as the concentration of solvent in the membrane gelation bath is increased. The composition of the membrane gelation bath varies with the nature of the solvent. Usually from about 10 to about 50 percent of solvent is present in the membrane gelation bath, with the balance being nonsolvent, preferably water together with whatever nonsolvent is employed in the casting resin solution, usually monocarboxylic acids containing 3 or 4 carbon atoms. For the solvents dimethylacetamide or N-methylpyrrolidone, the preferred concentration of solvent is from about 20 to about 45 percent. Organic solvents are the generally preferred additives to the membrane gelation baths.

OTHER CASTING PARAMETERS

Before casting membranes, it is preferred to filter the polymer solution. Filtration of the polymer solution before casting substantially reduces imperfections in the cast films. The solution can be suction filtered through glass microfiber, porous stainless steel or other filter material and then passed through one or more membranes laving pores with diameters of about five micrometers. In order to enable the solution to pass through the smaller pore size membranes at acceptable flow rates, it is usually necessary to apply pressure. The amount of pressure applied will depend upon the viscosity of the solution and the pore size of the membrane. Enough pressure to force the solution through the membrane is needed.

Degassing of the solution is important, as indicated previously, and may be accomplished through the use of any known technique.

The solution is then cast as a thin fluid film onto and/or into a suitable (porous or nonporous) substrate to form an overall membrane thickness of from about 25 to about 250 µm, preferably from about 50 to about 150 µm. Among the porous substrates which are useful for this invention are various non-woven and woven fabrics which are similar or identical to those used in the reverse osmosis and ultrafiltration industries. In addition to the flat sheet configuration, the membranes of this invention can be prepared in hollow fiber or tubular form with properties similar to those described for flat sheets.

Following gelation the membrane is washed free of solvent using water and dried.

The temperature of the casting or spinning solution is generally controlled in the range of between ambient and 85° C., preferably between 30° to 65° C., and the temperature of the coagulating liquid is generally controlled at about ambient.

GENERAL CHARACTERIZATION OF MEMBRANES

The pore sizes in the membranes of the present invention are in the range to produce molecular weight cutoff values of from about 1000 to about 500,000 daltons. The properties of the membranes may be determined by the specific properties of the selected polymer system employed, but with careful selection and good processing technique, it is possible to attain ultrafiltration membranes with physical and chemical properties appropriate for use in a wide variety of ultrafiltration and diafiltration operations.

The ultrafiltration membranes of the present invention are particularly desirable for use in diafiltration and ultrafiltration applications in biological systems.

Without limiting the breadth of the present invention, and without being bound to any particular theory, it is believed that the narrowness of the pore size distribution in membranes of the present invention is due to a number of related factors:

1.) the absence of extractable polymeric additives;
2.) the use of solvent vehicles containing large solvent entities;
3.) use of solutions with a low tolerance for nonsolvents;
4.) controlled nucleation of the solution by high sheer stirring, nonsolvent addition, and temperature control;
5.) removal of gel clumps from the solution by filtration, and high shear mixing;
6.) gelation of the casting solution in a nonsolvent bath which contains an appreciable concentration of solvent; and
7.) the ability to rapidly and accurately measure ultrafiltration pore size and membrane integrity by the $K_{UF}$ method and to make process changes in response to those measurements.

The ultrafiltration membranes of the present invention are particularly desirable for use for molecular separations, in diafiltration and ultrafiltration applications in biological systems.

By following the principles of the present invention, it is possible to make ultrafiltration/diafiltration membranes possessing the aforedescribed properties. The membranes of the present invention may also be characterized by their substantial freedom from major defects, such as pinholes or macrovoids that are in the form of finger-like intrusions extending from one surface of the membrane to the other. In some embodiments the membranes may also be characterized as consisting essentially of two layers, a thin skin with a narrow pore size distribution and a thick sponge-like, macrovoid free matrix. A third (transition) layer of intermediate density may also be found, between the skin and substructure layers.

THE NEW $K_{UF}$ METHOD OF CHARACTERIZATION

As discussed previously, there is currently no method of rapidly testing the integrity and molecular weight cutoff of an ultrafiltration membrane. What is needed in the case of ultrafiltration membranes is a test that can be implemented as rapidly and with the reliability of the $K_L$ and bubble point test methods as applied to microfiltration membranes. The bubble point test of a microfiltration membrane is measured by thoroughly and completely wetting the sample with a liquid and then pressurizing the upstream side of the membrane with air or other gaseous substance such as nitrogen. During the bubble point test the downstream side of the sample is observed visually as the upstream gas pressure is slowly increased. When the pressure has risen sufficiently a stream of bubbles is observed penetrating through the membrane. The pressure at which this stream of bubbles begins to flow is known as the initial bubble point. If the upstream air pressure is further increased, additional areas of the filter begin to show bubble streams until the entire sample appears to be foaming. The pressure at which this occurs is called the "FAO" or foam all over point. The significance of these measurements lies in the relationship between the pore size of the filter and the bubble point pressure, defined by the Laplace equation, $$\Delta P = 4\gamma/D$$

where
$\Delta P$=pressure difference across the medium
$\gamma$=surface tension of wetting fluid
D=diameter of the capillary or pore Although the pores of a filter may or may not be cylindrical in shape, the Laplace equation provides the theoretical basis for bubble point testing. Namely, the air or gas exerts a force on the pores or capillaries which are filled with the wetting liquid. When the pressure is large enough the liquid is pushed out and air flows freely through the once wetted pore of the filter. The air flow is observed downstream as a flow of bubbles. As can be seen from the Laplace equation, the smaller the diameter of the pore, the higher the pressure required to displace the liquid from the pore. Likewise, the higher the surface tension of the wetting fluid, the higher the pressure required to displace liquid from the pore.

The initial bubble point pressure is the pressure at which the bubble stream is first detected and thus corresponds to the opening of the largest pores of the membrane. Increasing the applied air pressure after observing the first bubble stream causes the liquid in progressively smaller pores to be displaced. The foam all over point is observed when the pressure is high enough to displace liquid from both the larger pores and from the smaller ones as well.

A refinement of the bubble point method is described in U.S. Pat. No. 4,340,479, which is incorporated herein by reference and is known as a $K_L$ measurement.

$K_L$ is an abbreviation for "knee location" a parameter of membrane behavior, designating the rated pore size of microfiltration membranes.

In the $K_L$ method, instead of simply observing the point at which a stream of bubbles begin to flow through the wetted media, the air flow rate through the wetted sample is measured downstream using a flowmeter. This allows one to obtain quantitative measurements of air flow vs air pressure. The shape of the curve is an indication of the broadness or narrowness of the pore size distribution arid the pressure at which the inflection in the curve occurs (the $K_L$ value) is a function of the membrane's pore size rating. The test is run by wetting the membrane with liquid and then slowly increasing the air pressure on the upstream side of the sample. A steady increase in air flow is measured downstream of the wetted sample as the pressure is increased. This is due to diffusive flow caused by the solubility of air in the wetting fluid. Finally, when the liquid begins to be displaced from the pores of the membrane the air flow rate increases rapidly due to bulk flow through the opened pores. By plotting air flow/air pressure on the Y axis instead of simply air flow, the pressure dependence of air solubility in the wetting fluid is masked. When the air or gas flow through a wetted membrane is plotted against increasing applied pressure, the initial flow is purely diffusive and the air flow per unit of applied pressure remains nearly constant, until a point is reached where a very small increment in pressure causes a very sharp rise in flow, such that the curve becomes nearly vertical. The pressure at which this occurs is designated as the $K_L$ for the membrane. The $K_L$ curve thus appears flat up to the inflection point. Uniform pore media are characterized by a sharp change in slope to a nearly vertical course at pressures above the $K_L$ valve.

The bubble point and $K_L$ liquid displacement techniques described above are useful for characterizing membranes and other filter materials having pore sizes down to around 0.05 μm in diameter. Although the $K_L$ test is an excellent way to test microfiltration membranes, such a test will not work for ultrafiltration membranes, because the high pressure that would be required to displace the wetting fluid from the ultrapores in the ultrafiltration membrane would compress or crush the membrane. Thus, unfortunately, there presently is no good way to test the integrity of an ultrafiltration membrane, and certainly no rapid way to do so.

$K_L$ type measurements may be made on membranes having pore ratings down to about 0.05 μm by using low surface tension wetting liquids, such as ethyl alcohol, with a liquid/air surface tension of about 24 dynes/cm. Examination of the Laplace equation shows the dependance of displacement pressure on surface tension (γ). As the surface tension of the wetting fluid decreases, the pressure required to displace fluid from a capillary or pore also decreases. However the air/liquid and vapor/liquid surface tensions are too high to be useful for conventional bubble point or $K_L$ testing of membranes having very small pore sizes. Although some fluorocarbon fluids have liquid/air surface tensions between 12 and 18 dynes/cm such a level is still too high to be of use.

In conjunction with the present invention, a method for characterizing membranes is provided. The method comprises thoroughly wetting the membrane to be tested with an initial wetting liquid that is capable of fully wetting the membrane, placing a displacing liquid in contact with one side of the wetted membrane, applying increasing pressure to said displacing liquid; and measuring the flow rate of liquid that passes through said membrane as a function of the applied pressure; wherein the displacing liquid is substantially insoluble in the wetting liquid and the interfacial tension between the wetting liquid and the displacing liquid is about 10.0 dynes/cm or less. This allows for the elimination of the high surface tension air/liquid interface formed during conventional bubble point or $K_L$ testing. Instead, a low interfacial tension liquid/liquid interface is formed which permits test pressures to be decreased by thousands of psi. For example, it is estimated that water wet ultrafiltration membranes would require conventional $K_L$ test pressures that, depending on the rated molecular weight cutoff, could be higher than about 5000 psi. By using the $K_{UF}$ test method, test pressures can be reduced to below about 120 psi depending on the choice of immiscible fluids.

For the purpose of describing the new $K_{UF}$ test method, "fluid A" will be used to describe the liquid with which the membrane is wetted (also referred to as the "wetting liquid"). "Fluid B" (also referred to as the "displacing liquid") will be used to describe the liquid that is used to displace fluid A from the pores of the membrane. Fluids A and B must be essentially immiscible liquids.

The test is performed by wetting a membrane with fluid A which must be capable of thoroughly wetting the membrane. The sample is then assembled into a test jig in which fluid B contacts the upstream side of the fluid A wetted membrane. The downstream side of the jig is connected via tubing to the side arm of a filtration flask or other suitable vessel capable of collecting fluid expressed downstream of the membrane (see FIG. 1). The side arm flask is stoppered with a one hole stopper into which a flowmeter is inserted. Thus, any fluid entering the side arm of the filtration flask will begin to fill the flask and in the process vent air contained in the flask through the flowmeter. This arrangement permits the measurement of the fluid B flow rate through the fluid A wetted membrane by means of the rate at which air is displaced from the side arm flask. The fluid B flow rate could be measured directly as liquid flow but implementation of such a measuring technique would be unnecessarily more complicated.

In running the $K_{UF}$ test, pressure is applied to the reservoir containing fluid B while fluid flow is monitored downstream of the membrane using the flowmeter. Air will only flow out through the flow meter if liquid is expressed downstream of the membrane. Liquid can only penetrate the sample if the pressure applied to fluid B is sufficient to displace fluid A from the pores of the membrane. The pressure required to displace fluid A from the pores of the membrane is a function of the pore diameter. Hence the measured pressure required to establish fluid flow through the membrane is dependent on the pore size and thus the molecular weight cutoff of the ultrafiltration membrane. As the pressure applied to fluid B is increased, flow is established through an increasing fraction of the smaller pores of the membrane. If the pore size distribution of the membrane is narrow, a small pressure increase will result in a large increase in fluid B flow through the membrane. This is evidenced by an inflection point in the flow rate vs pressure curve. At pressures below the inflection point the curve is basically horizontal provided that time membrane has pores of relatively uniform diameter. Once the pressure has been increased sufficiently beyond the inflection point, the flow rate increases rapidly and for a membrane with a narrow pore size distribution, the curve becomes almost vertical. The narrower the pore size distribution the steeper the slope of the vertical lying portion of the curve.

The pressure needed to displace fluid A from the membrane depends on the interfacial tension between the immiscible fluids A & B as well as on the pore diameter of the membrane. By choosing fluids A & B such that the interfacial tension is small, for example the 1-butanol/water system with an interfacial tension of about 1 or 2 dynes/cm, the test pressures can be kept relatively low, even for UF membranes with extremely small pore diameters. Finally, by plotting fluid B pressure vs. downstream flow, a curve similar to a $K_L$ curve is obtained. In the test procedure the air flow vented from the flask is measured using a flowmeter or flow transducer. Any suitable method of measuring the fluid flow, however, may be used.

Fluid systems consisting of pairs of immiscible liquids in which both fluids are in contact with one another and thus forming a phase boundary between the layers, are known to have very low interfacial tensions. Interfacial tensions in this case are measured between the liquid phases at the boundary between the two immiscible liquids. Table 1 is a listing of interfacial tensions for several organic liquids that form a phase boundary with water as reported in the book Interfacial Phenomena, $2^{nd}$ ed., by J. T. Davies, and E. K. Rideal (1963). Also included in Table 1 are solubilities of the various compounds in water as reported in the Chemical Rubber Handbook (CRC), 1970 ed.

TABLE 1

| COMPOUND | INTERFACIAL SURFACE TENSION dynes/cm | TEMP °C. | SOLUBILITY (g/100 g $H_2O$) |
|---|---|---|---|
| ethyl ether | 10.7 | 20 | 7.5 |
| n-octanol | 8.5 | 20 | 0.054 |
| n-hexanol | 6.8 | 25 | |
| | | 20 | 0.6 |
| aniline | 5.85 | 20 | |
| n-pentanol | 4.4 | 25 | |
| | | 22 | 2.7 |
| ethyl acetate | 2.9 | 30 | |
| | | 15 | 8.5 |
| isobutanol | 2.1 | 20 | |
| | | 15 | 10.0 |
| n-butanol | 1.8 | 25 | |
| | 1.6 | 20 | |
| | | 15 | 9.0 |

Although the Table 1 lists only organic liquids and water, the $K_{UF}$ test method described above can be performed using any pair of immiscible liquids.

In accordance with the foregoing method, the wetting liquid may be a single liquid compound, such as n-octyl alcohol, and the displacing liquid also may be a single compound, such as water, which is substantially insoluble in the n-octyl alcohol. Alternatively, the wetting liquid may be an equilibrium mixture comprising a first liquid compound, such as n-butyl alcohol, that is saturated with a second liquid compound, such as water. The second liquid compound, saturated with the first, is then used as the displacing liquid. With respect to either embodiment, the important fact is that the interfacial tension between the two liquids remains relatively constant while performing the test. It is thus recommended that the phases be compositionally stable, i.e., when the phases are in contact no net flux of fluid A occurs across the interface and no net flux of fluid B occurs across the interface. Thus, there is no substantial variation in the solubility of the displacing liquid in the wetting liquid, which, if present, could affect the results.

Furthermore, it is important that the interfacial tension between the wetting liquid and the displacing liquid be not more than about 10.0 dynes/cm, preferably not more than about 2.0 dynes/cm, and most preferably not more than about 1.6 dynes/cm.

In practice the $K_{UF}$ test is usually run with each of the immiscible phases saturated with the fluid in which it is in intimate contact. For example, Table 1 gives the solubility of 1-butanol in water as 9.0 g per 100 g of water at 15° C. Since some 1-butanol will dissolve in water it is preferred that the water phase be saturated with n-butanol. Likewise with the 1-butanol phase, it is preferred that it be saturated with water. Mutually saturated phases are easily achieved by shaking a mixture containing sufficient quantities of each of fluids A and B together in a container or separatory funnel. In the tests and examples described herein, the organic phase was in each case used as fluid A to wet the membrane and fluid B was the aqueous phase. It is an obvious extension of the method to reverse the fluids, i.e., wetting the membrane with the aqueous phase and pressurizing the upstream side of the membrane with the organic phase.

FIGS. 3-7 are diagrams illustrating the $K_{UF}$ curve and the $K_{UF}$ characteristic pressure obtained by following the test procedure just described. The $K_{UF}$ characteristic pressure of the membrane is obtained by extrapolating a line along the steep portion of the test curve down to the horizontal axis and reading the pressure, again the aforementioned Figures illustrate the method. The $K_{UF}$ characteristic pressure, then, is a measure of the molecular weight cutoff for the membrane, as defined in FIG. 2, the details regarding the generation of which are explained in Example 14.

The advantage of using the $K_{UF}$ method is that ultrafiltration and microporous membranes of almost any pore size, large or extremely small, can be characterized rapidly using test pressures generally below about 120 psig and often below 100 psig.

EXAMPLES

Examples 1–9

A mixture of N,N-dimethylacetamide (DMAC) and propionic acid (PA) in a ratio of between 1.5 to about 2.0 parts of DMAC to one part of PA was used to dissolve polyethersulfone resin (Ultrason E6010, BASF) at 17% solids, by weight. The polyethersulfone resin was combined with the DMAC/PA solvent system in a water jacketed resin kettle and maintained at a constant temperature of 50° C. while mixing for not less than 16 hours. The resulting solution was allowed to cool to room temperature during which time it was filtered and then deaerated under vacuum.

Figure 3:
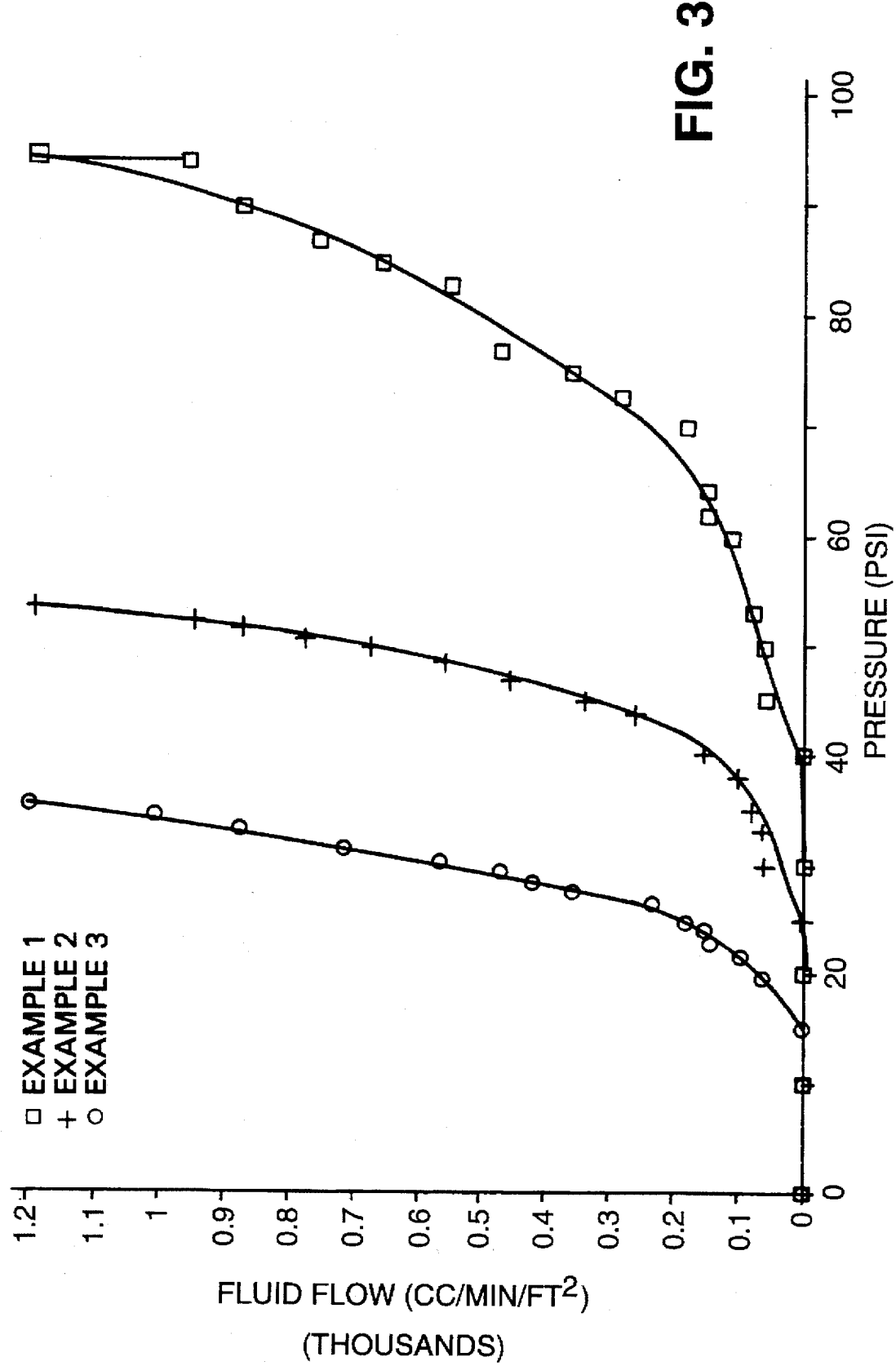
FIG. 3 is a graph showing the $K_{UF}$ plots for Examples 1 through 3 of the present invention.
Figure 4:
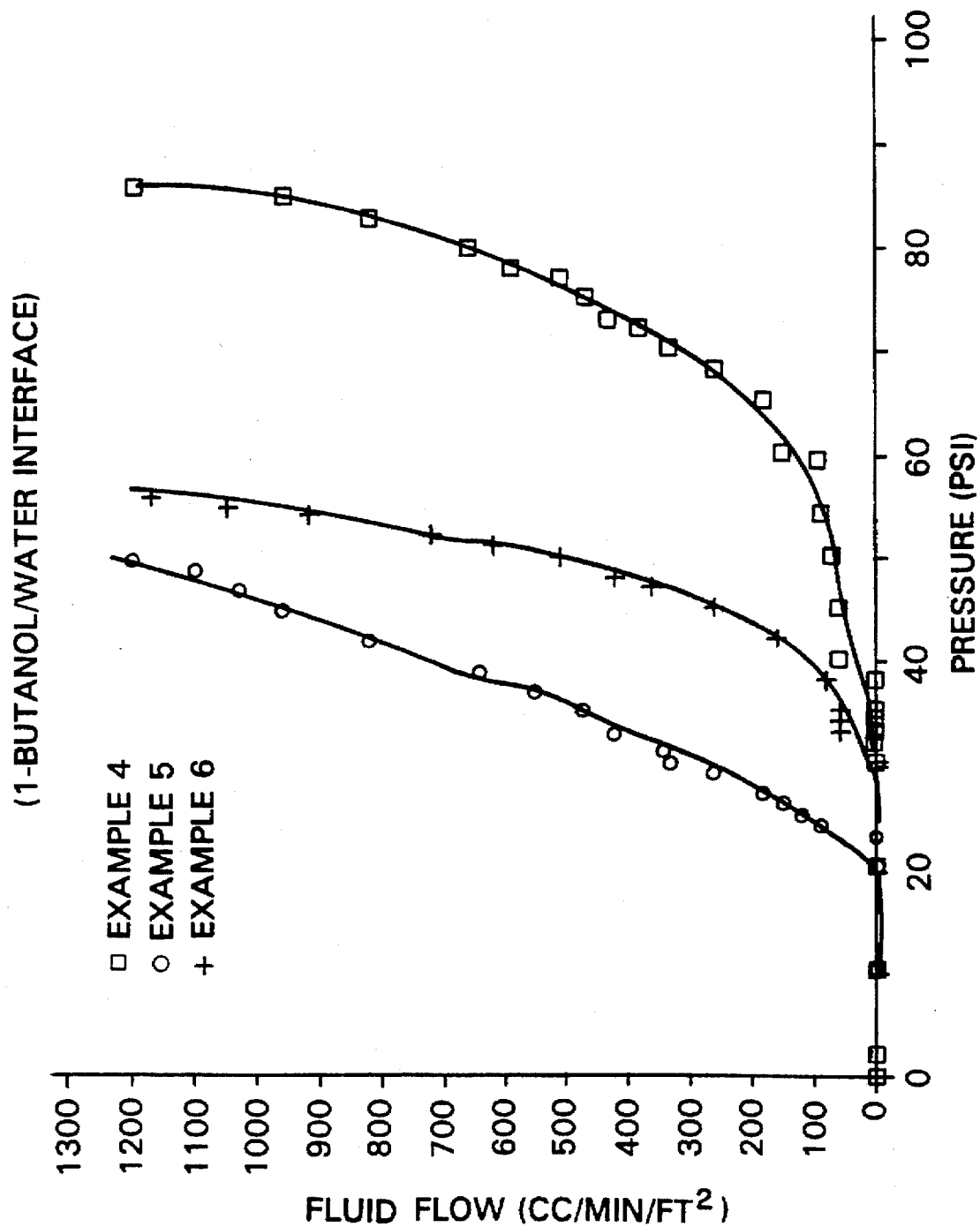
FIG. 4 is a graph showing the $K_{UF}$ plots for Examples 4 through 6 of the present invention.
Figure 5:
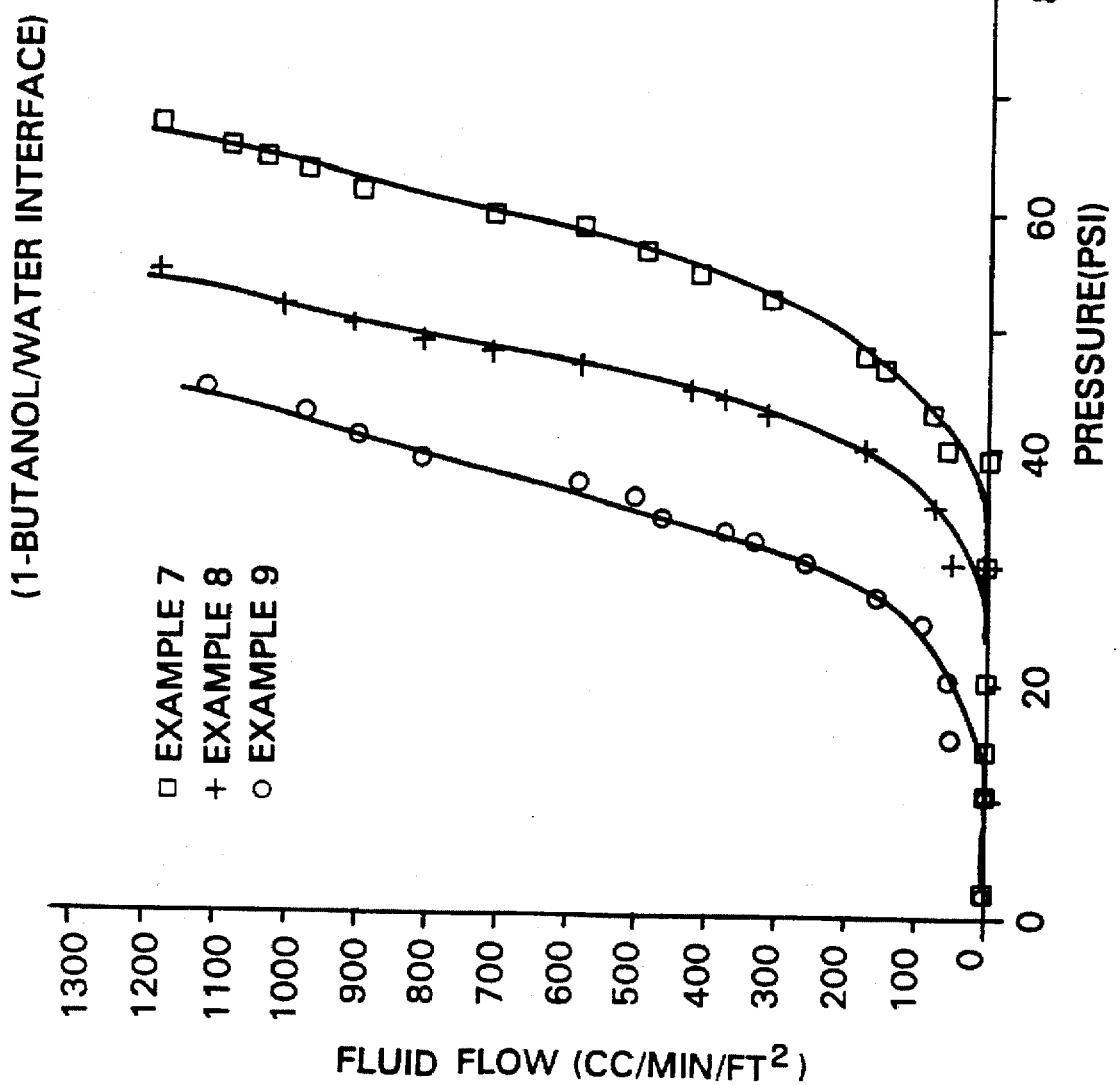
FIG. 5 is a graph showing the $K_{UF}$ plots for Examples 7 through 9 of the present invention.
Figure 8:
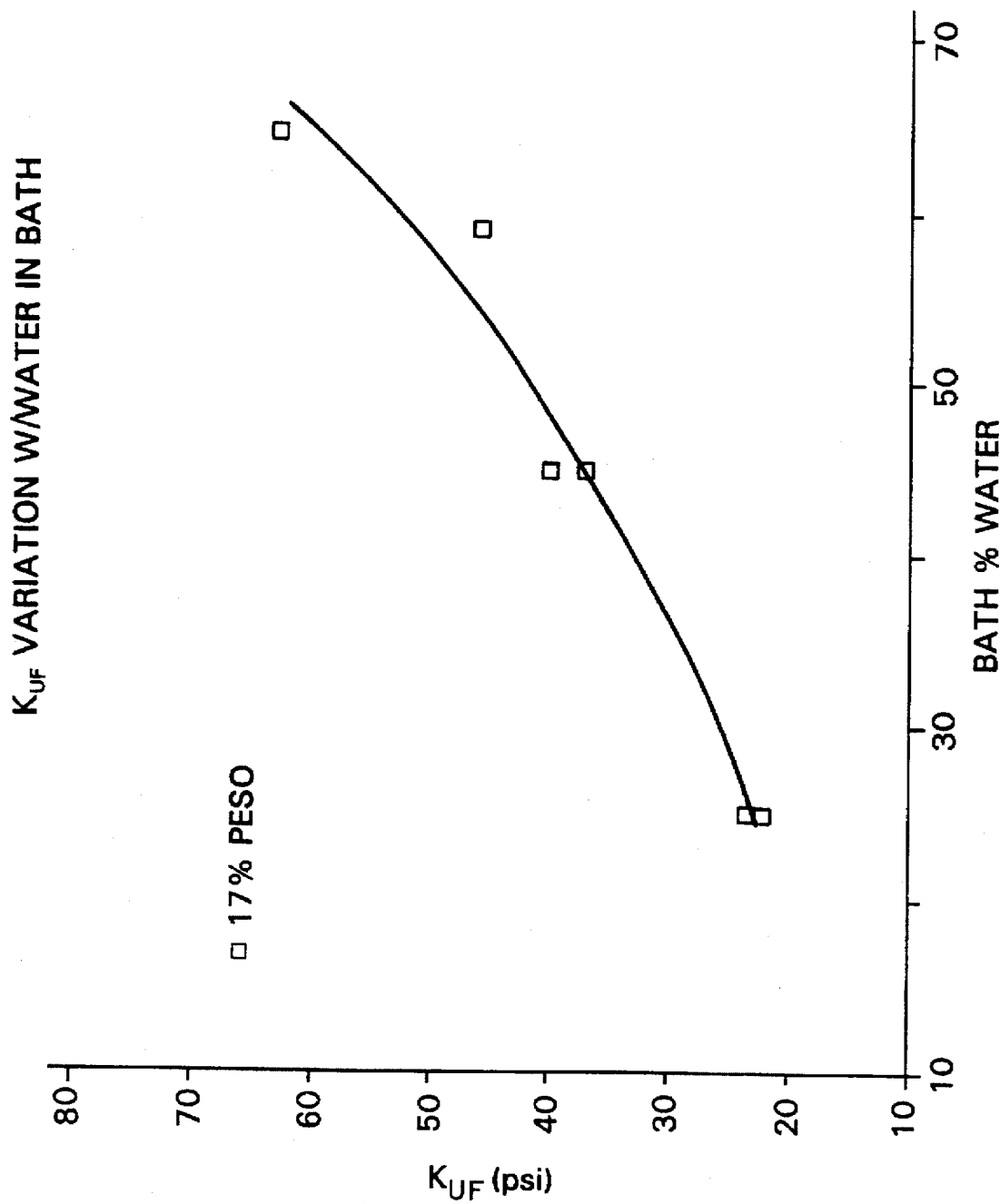
FIG. 8 is a graph showing the relationship between the concentration of nonsolvent in the casting bath and resulting $K_{UF}$ values of the membranes.

A quantity of the resin solution sufficient for doctoring a film having dimensions roughly 5 mils thick×10 inches long×8 inches in width was applied to a glass plate and a film was drawn. The glass plate containing the drawn film was then immersed in a setting bath containing a mixture of DMAC, PA and water. Setting bath compositions were such that the ratio of DMAC:PA was the same in the bath as in the casting resin solution. The concentration of water in the setting baths was varied between 25 and 65% by weight with the balance of the bath composed of DMAC and PA. After the membrane had set it was removed from the bath, water washed, and dried in an oven at a temperature of 100° C. for about 10 minutes. Table 2 lists a set of casting resin and bath compositions along with the $K_{UF}$ characteristic pressures and molecular weight cutoffs for membranes prepared using the procedure described above. All $K_{UF}$ data appearing in this document was obtained at ambient temperature using 1-butanol saturated with water as the wetting fluid and water saturated with 1-butanol as the displacing fluid. FIGS. 3 through 5 are the $K_{UF}$ curves measured for each sample. As can be seen from the $K_{UF}$ curves, for any particular casting resin composition, the pore size of the membrane can be varied by varying the concentration of water in the bath. This is illustrated in FIG. 8.

By using the $K_{UF}$ test method it is shown that the membranes of the present invention, as illustrated by Examples 1–9, had $K_{UF}$ values within the range from about 10 psi to about 100 psi.

Examples 10–12

A master resin solution was prepared by dissolving polyethersulfone resin (Ultrason E6010, BASF Corporation) at a concentration of 25.85% solids in dimethylacetamide ("DMAC") at a temperature of 65° C. The master resin solution was then mixed under high shear conditions using a Type PT45/80 Polytron® mixer (Kinematica GmbH, Switzerland) distributed in the U.S. by Brinkmann Instruments, Westbury, N.Y. 11590, to break up any undissolved polymer gels by mixing for about 1 minute at a high speed during which time the master resin temperature increased to about 80° C.

A quantity of the master resin solution, 393.2 g, was transferred to a water jacketed-flask. The resin temperature was controlled in the flask at 65° C. during which time 171.6 grams of propionic acid was added to the transferred resin while mixing with a propeller type agitator. This resulted in a casting solution containing 18% polyethersulfone resin, 51.6% DMAC and 30.4% PA.

The above solution was permitted to mix at 65° C. for about one half hour using the propeller type agitator.

Figure 6:
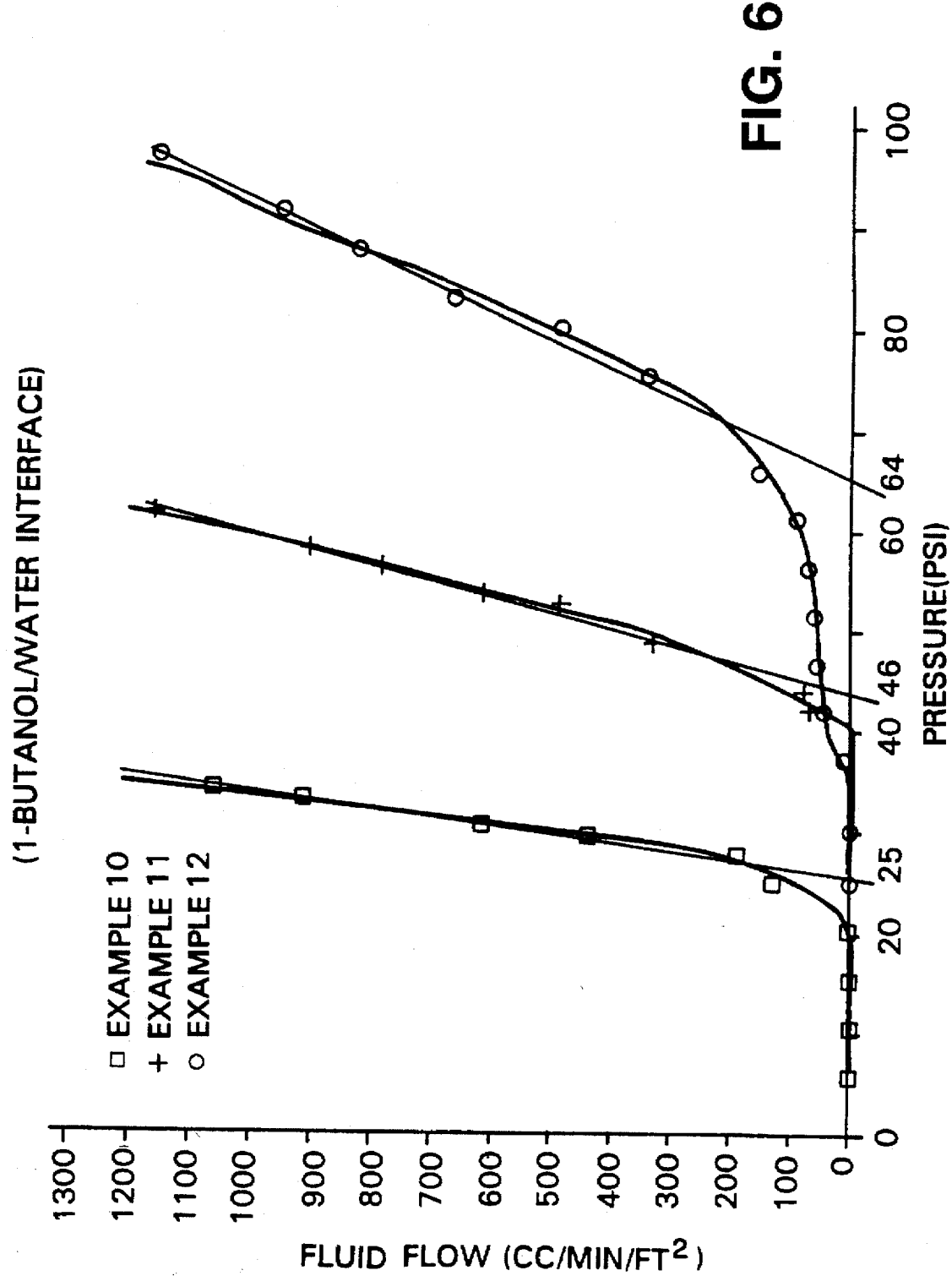
FIG. 6 is a graph showing the $K_{UF}$ plots for Examples 10 through 12 of the present invention.

The casting solution was then, allowed to cool to 30° C. over a 2 hour period while mixing slowly. The casting resin solution was then removed from the jacketed flask and mixed with the Polytron mixer for about 40 sec during which time the temperature increased to 55° C. The solution was then filtered through a 5 μm nylon membrane. The resin was allowed to cool to room temperature and was then deaerated. Samples were cast into setting baths containing 25, 45 and 65% water, with the balance of the bath being composed of DMAC and PA in a ratio of 1.7 parts of DMAC, by weight, to 1 part of PA. Table 3 summarizes the casting conditions and FIG. 6 is a graph of the resulting $K_{UF}$ curves for the membranes. By varying the resin concentration of the casting solution in the range between about 15 and 20% solids while maintaining a ratio of DMAC:PA of between 1.5 and 2 and using the $K_{UF}$ test method, it is shown, that the membranes of the present invention had $K_{UF}$ values from about 10 to 100 psi when tested using 1-butanol saturated with water as the wetting fluid and water saturated with 1-butanol as the displacing liquid. Varying the concentration of water in the bath will vary the pore size of the membrane and hence the $K_{UF}$ characteristic pressure and molecular weight cutoff of the membrane.

TABLE 2

UF - Membranes Castings Examples 1–9

| | Casting Solution Parameters | | | Casting Bath | | | Membrane Parameters $K_{UF}$ | | |
|---|---|---|---|---|---|---|---|---|---|
| Example | % PES | % DMAC | % PA | % H₂O | % DMAC | % PA | (psi) | MWCO | Remarks |
| 1 | 17 | 52 | 31 | 65 | 22 | 13 | 63 | 18K | DMAC:PA = 1.7:1 |
| 2 | 17 | 52 | 31 | 45 | 35 | 20 | 40 | 45K | solvent |
| 3 | 17 | 32 | 31 | 25 | 47 | 28 | 22 | 106K | nonsolvent ratio Solution cast at room temp. |
| 4 | 17 | 55 | 28 | 65 | 23 | 12 | 63 | 18K | DMAC:PA = 1.92:1 |
| 5 | 17 | 55 | 28 | 45 | 36 | 19 | 40 | 45K | solvent |
| 6 | 17 | 55 | 28 | 25 | 49 | 25 | 22 | 106K | nonsolvent ratio Solution cast at room temp. |
| 7 | 17 | 50 | 33 | 59 | 25 | 16 | 46 | 36K | DMAC:PA = 1.5:1 |
| 8 | 17 | 50 | 33 | 45 | 33 | 22 | 37 | 51K | solvent |
| 9 | 17 | 50 | 33 | 25 | 45 | 30 | 23 | 100K | nonsolvent ratio Solution cast at room temp. |

TABLE 3

UF - Membranes Castings Examples 10–12

| | Casting Solution Parameters | | | Casting Bath Parameters | | | Membrane Parameters $K_{UF}$ | | |
|---|---|---|---|---|---|---|---|---|---|
| EXAMPLE | % PES | % DMAC | % PA | % H₂O | % DMAC | % PA | (psi) | MWCO | Remarks |
| 10 | 18 | 52 | 30 | 25 | 47 | 28 | 25 | 90K | DMAC:PA = 1.7:1 solvent:non-solvent ratio Solution cast at room temperture |
| 11 | 18 | 52 | 30 | 45 | 35 | 20 | 43 | 40K | |
| 12 | 18 | 52 | 30 | 65 | 22 | 13 | 64 | 18K | |

EXAMPLE 13

Samples of commercial ultrafiltration membranes, all with molecular weight cutoffs rated at or below 10,000, were compared with a membrane of this invention with a molecular weight cutoff rating of 18,000. The abilities of the various ultrafiltration membranes to exclude 0.020 and 0.038 µm diameter monodisperse latex spheres were compared using the following procedure. The ability to exclude such particles is understood to mean that such exclusion is measured to the detection limits of the present analysis which is approximately $4.5 \times 10^9$ particles per ml for a 0.038 µm diameter latex and $4.5 \times 10^{10}$ particles per ml for a 0.02 µm latex. Should more precise measuring techniques be employed, and show that total exclusion is not achieved, such a fact would not alter the definition of exclusion as used in the present invention which is to be understood to mean total exclusion to the detection limits of the procedure as defined in this example.

A Tween 20 surfactant solution was prepared by heating 500 ml of deionized water to 60° C. and adding 0.5 ml of Tween 20 surfactant, with stirring for 10 minutes. The solution was cooled and subsequently used as a dispersing medium for monodisperse latex particles.

Monodisperse latex beads of 0.02 µm diameter were dispersed in the Tween 20 surfactant solution at a concentration of 0.01% latex solids which corresponds to a number concentration of about $2.3 \times 10^{13}$ particles per ml. This solution was prepared by adding 0.5ml of 2% latex as supplied by Duke Scientific, the distributor, to 99.5 ml of the Tween 20 surfactant solution with stirring. A similar 0.01% latex solids dispersion was prepared using 0.038 µm diameter latex beads manufactured by Dow and the Tween 20 surfactant solution. A 0.01% dispersion of the 0.038 µm latex corresponds to a number concentration of about $3.3 \times 10^{12}$ particles per ml of dispersion.

Ultrafiltration membranes were then tested as 25 mm disks for penetration of latex particles through the sample during filtration tests of the 0.01% latex dispersions. Also one hollow fiber module manufactured by A/G Technology Corporation, was so tested as described below.

To prepare commercial membranes for testing the manufacturer's instructions regarding the removal of humectant prior to membrane usage were applied. This consisted of soaking the sample for a period of about 1 hour. in Tween 20 solution which was free of latex, during which time the fluid was changed 3 times. Soaking the membranes of this invention and the A/G hollow fiber module was not required since they contain no humectant. Membranes were then inserted into a 25 mm disk holder and a 5 cc syringe was filled with the 0.01% latex suspension. The fluid was forced through the filter and collected in glass vials. In the case of the A/G hollow fiber sample, the module was tested with the 0.01% latex dispersion using the testing procedure described by the manufacturer in the product literature.

Figure 9A:
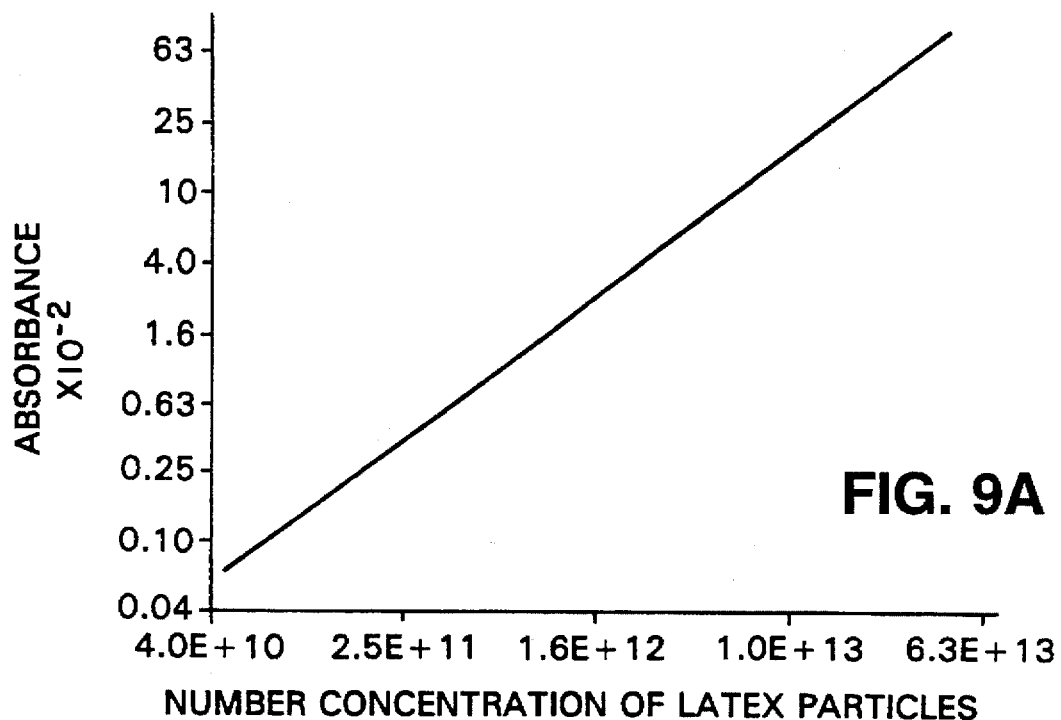
FIGS. 9A and 9B are graphs showing the relationship between UV absorbance and monodisperse latex bead concentration, as used to determine the exclusion coefficient for ultrafiltration membranes, in accordance with the present invention for 0.02 µm latex particles (FIG. 9A) and for 0.038 µm latex particles (FIG. 9B).
Figure 9B:
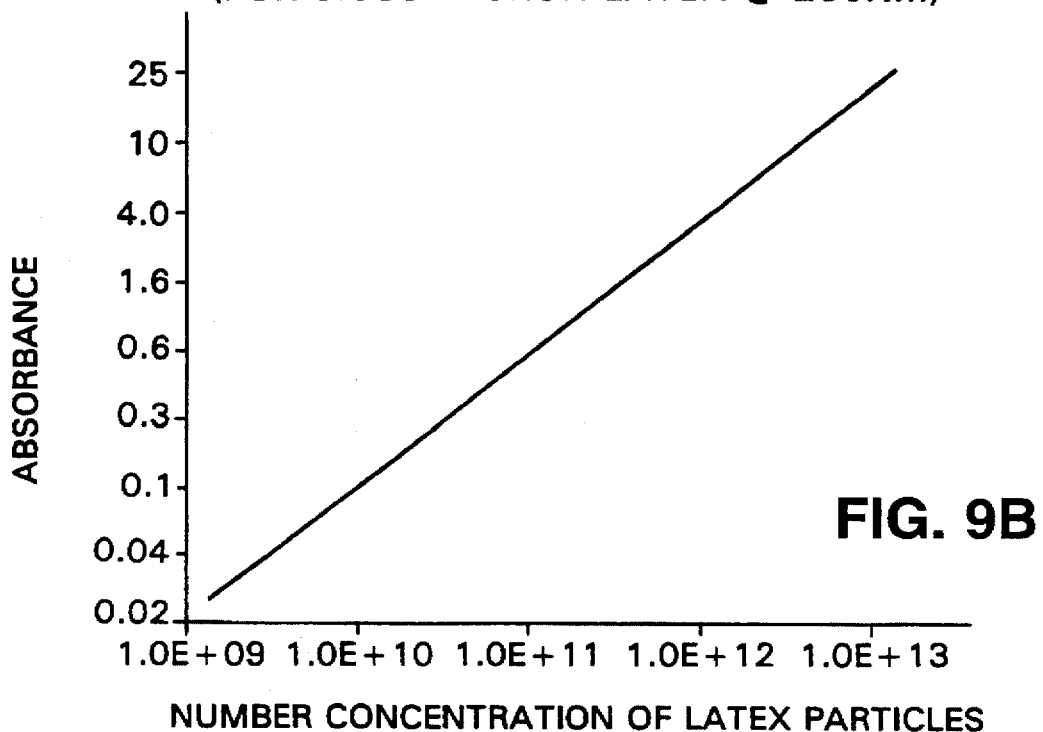
Figure 10A:
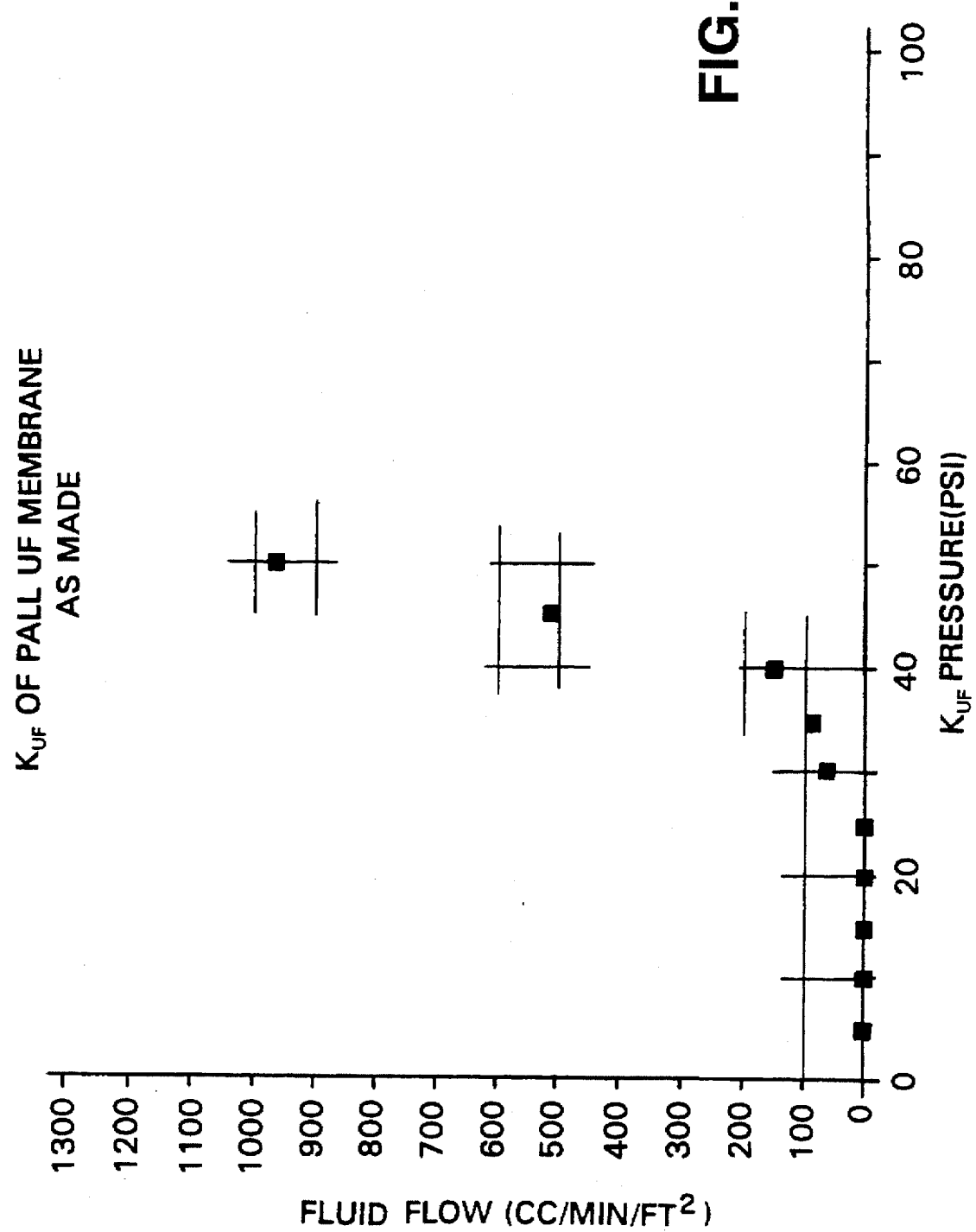
FIGS. 10A and 10B are $K_{UF}$ graphs for a membrane of the present invention comparing the $K_{UF}$ curve shape before (FIG. 10A) and after (FIG. 10B) 1 wet/dry cycle.
Figure 10B:
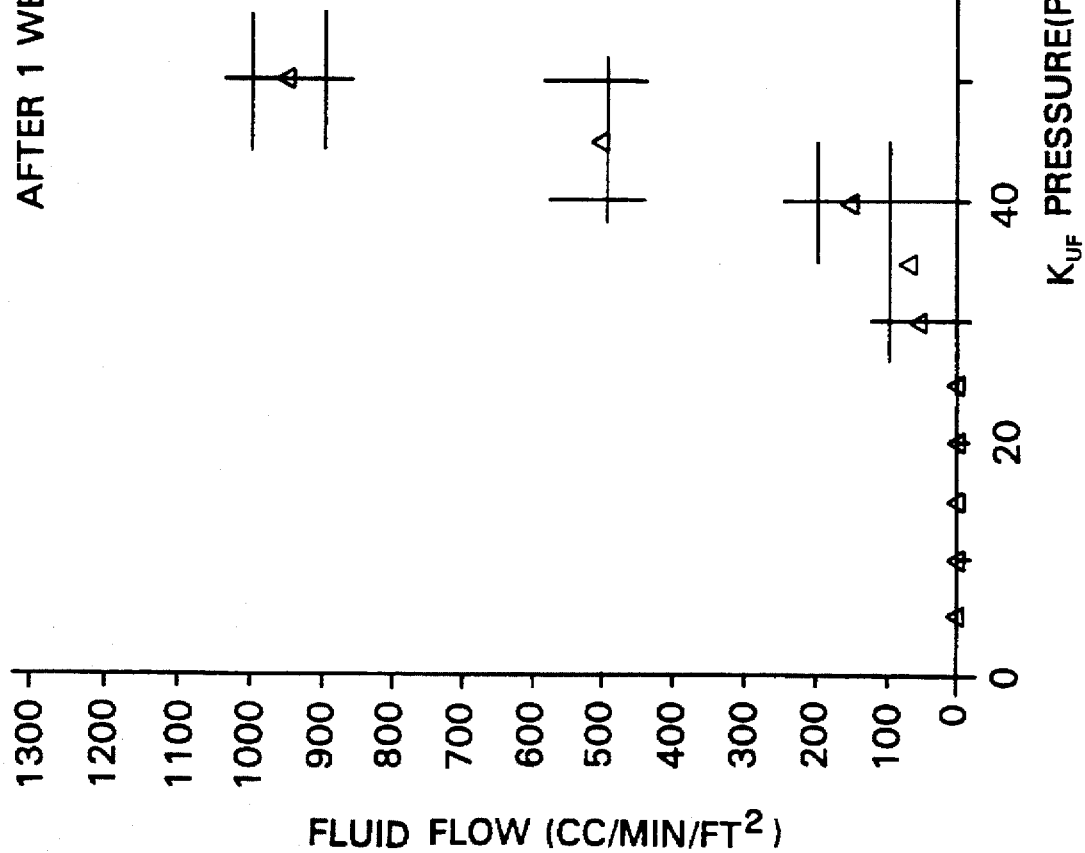

The number concentration of latex particles found in the effluents was determined by measuring the UV absorbance at a wavelength of 250 nm relative to a latex free Tween 20 solution. The effluent latex concentration was determined from the calibration curves of FIGS. 9A and 9B, in which absorbance is plotted vs the number concentration of latex particles i.e., 0.02 µm latex particles in FIG. 9A and 0.038 µm latex particles in FIG. 9B.

Rejection coefficients for latex particles were determined using the following formula:
Rejection Coefficient=1−[F/I] where, F=number concentration of latex particles detected in effluent I=initial number concentration of latex particles with which upstream side of membrane was challenged Latex exclusion tests were also run on samples that were wet/dry cycled prior to the latex particle challenge. A wet/dry cycle consisted of flushing water through the membrane, drying the sample, re-wetting the sample with ethyl alcohol, again flushing water through the sample to remove the alcohol and finally drying. This was repeated 3 times on a number of samples as indicated in Table 4, after which the membrane was challenged with latex as described earlier. The results of the latex exclusion tests are contained in Table 4.

TABLE 4

Latex Challenge

| Sample Type | MWCO | No. of wet/dry cycles | Particle Diameter (µm) | Input Conc. No./ml | Effluent Conc. No./ml | Rejection Coeff. |
|---|---|---|---|---|---|---|
| Amicon PM10 | 10K | 0 | 0.02 | $2.3 \times 10^{13}$ | $1.3 \times 10^{12}$ | 0.94 |
| Filtron Omega | 10K | 0 | 0.02 | $2.3 \times 10^{13}$ | $2.2 \times 10^{12}$ | 0.90 |
| Millipore PTGC 10 | 10K | 0 | 0.02 | $2.3 \times 10^{13}$ | none detected | >.998 |
| Millipore PTGC 10 | 10K | 3 | 0.02 | $2.3 \times 10^{13}$ | $2.1 \times 10^{13}$ | 0.09 |
| Millipore PTGC 10 | 10K | 3 | 0.038 | $2.3 \times 10^{13}$ | $1.3 \times 10^{12}$ | 0.61 |
| AG Hollow Fiber UFP-5-C-4 | 5K | 0 | 0.02 | $2.3 \times 10^{13}$ | $8.9 \times 10^{11}$ | 0.96 |
| Pall Membrane of Example 12 | 18K | 3 | 0.02 | $2.3 \times 10^{13}$ | none detected | >.998 |

The foregoing results clearly show that the membranes of the present invention can be wet/dry cycled and will still retain the ability to exclude 0.02 µm particles. None of the commercially available ultrafiltration membranes including the Millipore sample referenced in Example 13 above, was able to exclude 0.02 µm particles after the membranes were wet/dry cycled. In fact the Millipore PTGC 10 membrane was shown to pass even 0.038 µm particles after wet/dry cycling. Additionally, most of the samples listed in Table 4, with the exception of the Millipore PTGC 10 and the membranes of the present invention, cannot exclude 0.02 µm latex particles even when they have not been wet/dry cycled at all.

EXAMPLE 14

Figure 2:
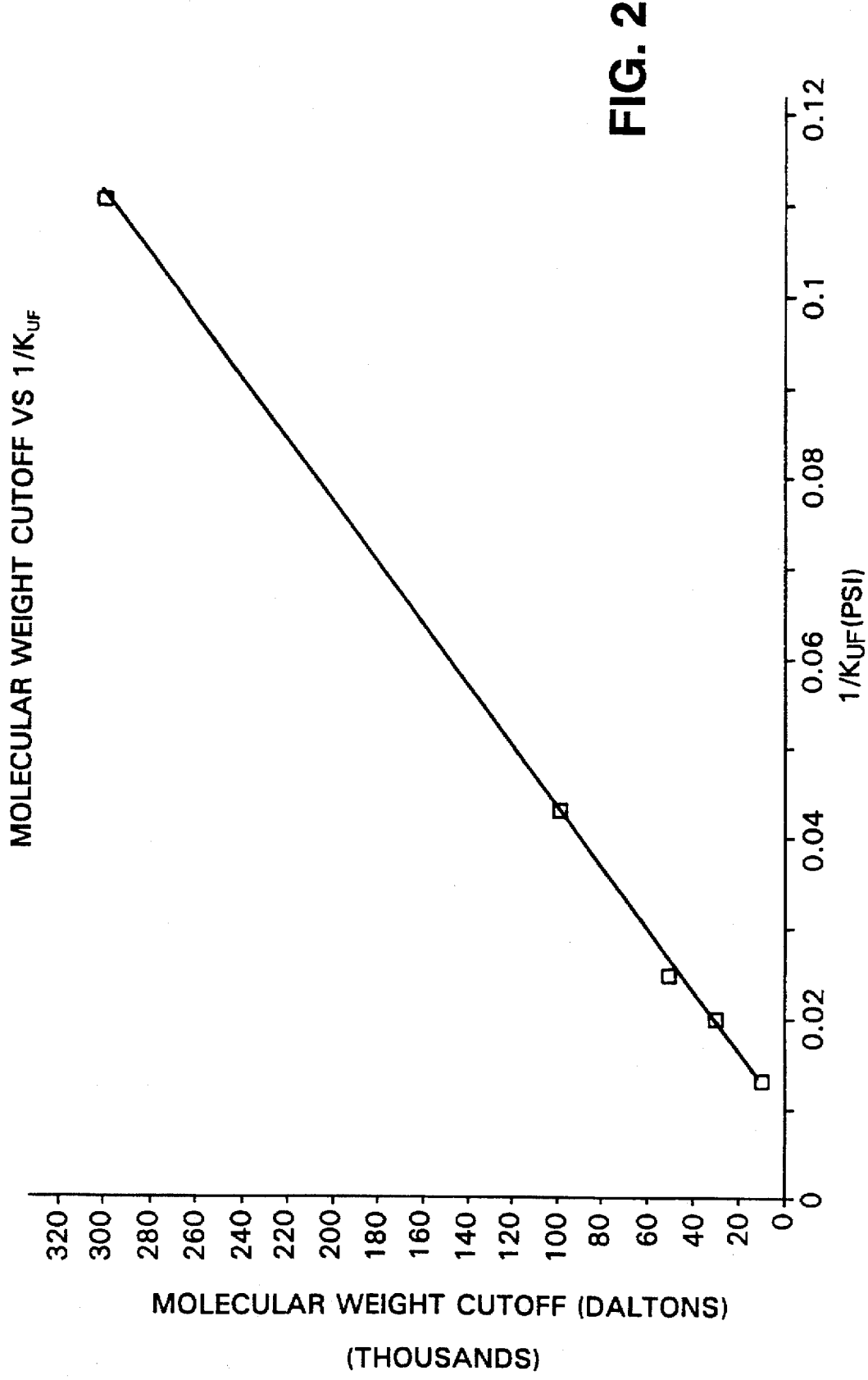
FIG. 2 is a graph showing the correspondence between molecular weight cutoff and the reciprocal of $K_{UF}$ values determined in accordance with the present invention.
Figure 7:
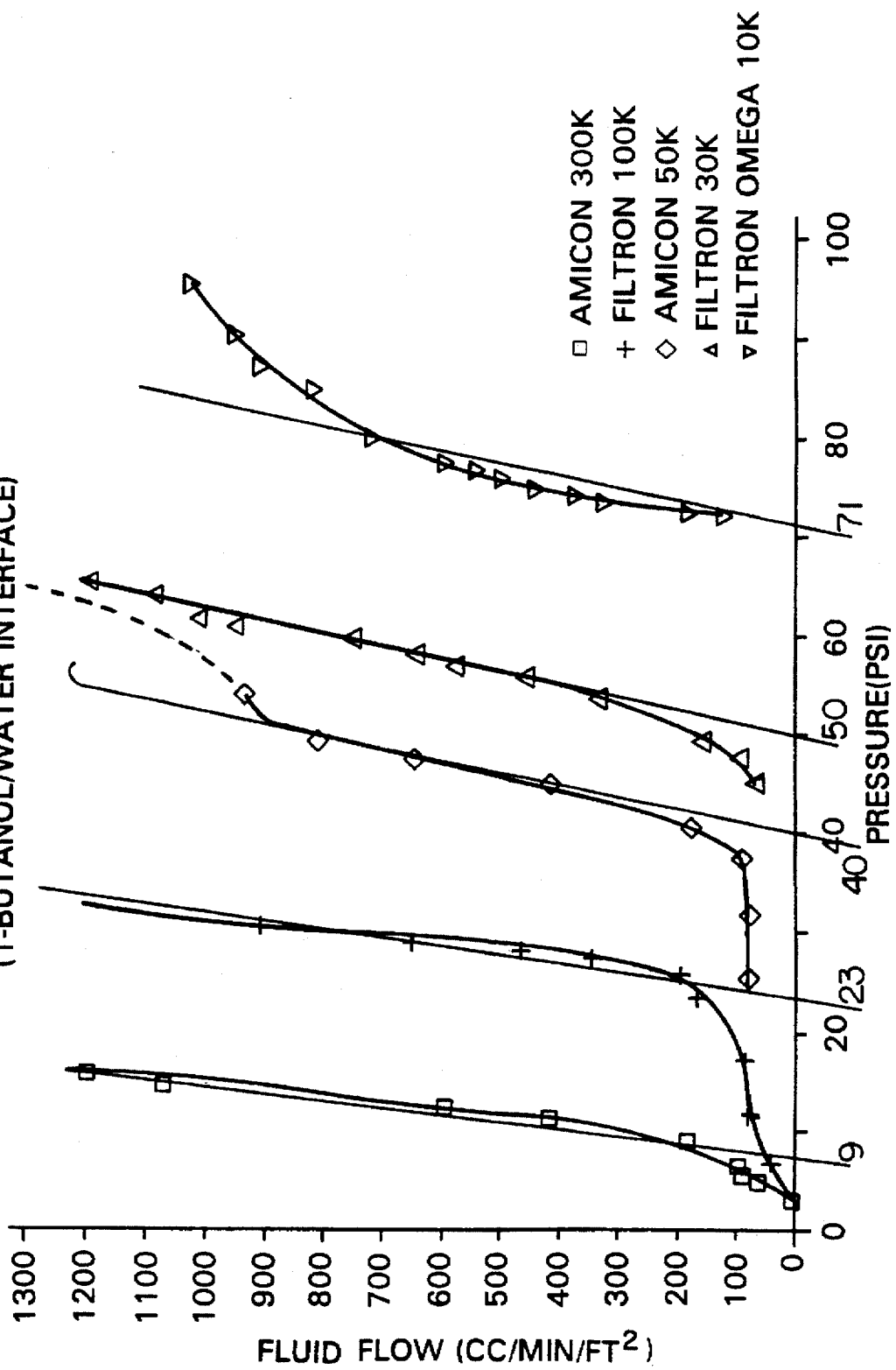
FIG. 7 is a graph showing the $K_{UF}$ plots for several commercial ultrafiltration membranes.

FIG. 7 was obtained by measuring the $K_{UF}$ curves for a variety of commercially available UF membranes. The $K_{UF}$ characteristic pressures of these samples were determined from the curves of FIG. 7 using the method described earlier. Table 5 lists the $K_{UF}$ values so obtained along with the rated molecular weight cutoffs for the membranes. FIG. 2 was obtained by taking the data from Table 5 and plotting the molecular weight cutoff vs. $1/K_{UF}$. As can be seen from the graph the result is a linear relationship that permits the determination of the molecular weight cutoff by simply measuring the $K_{UF}$ characteristic pressure of the membrane. The $K_{UF}$ test thus represents a major advance in the characterization and integrity testing of ultrafiltration membranes.

EXAMPLE 15

Figure 11B:
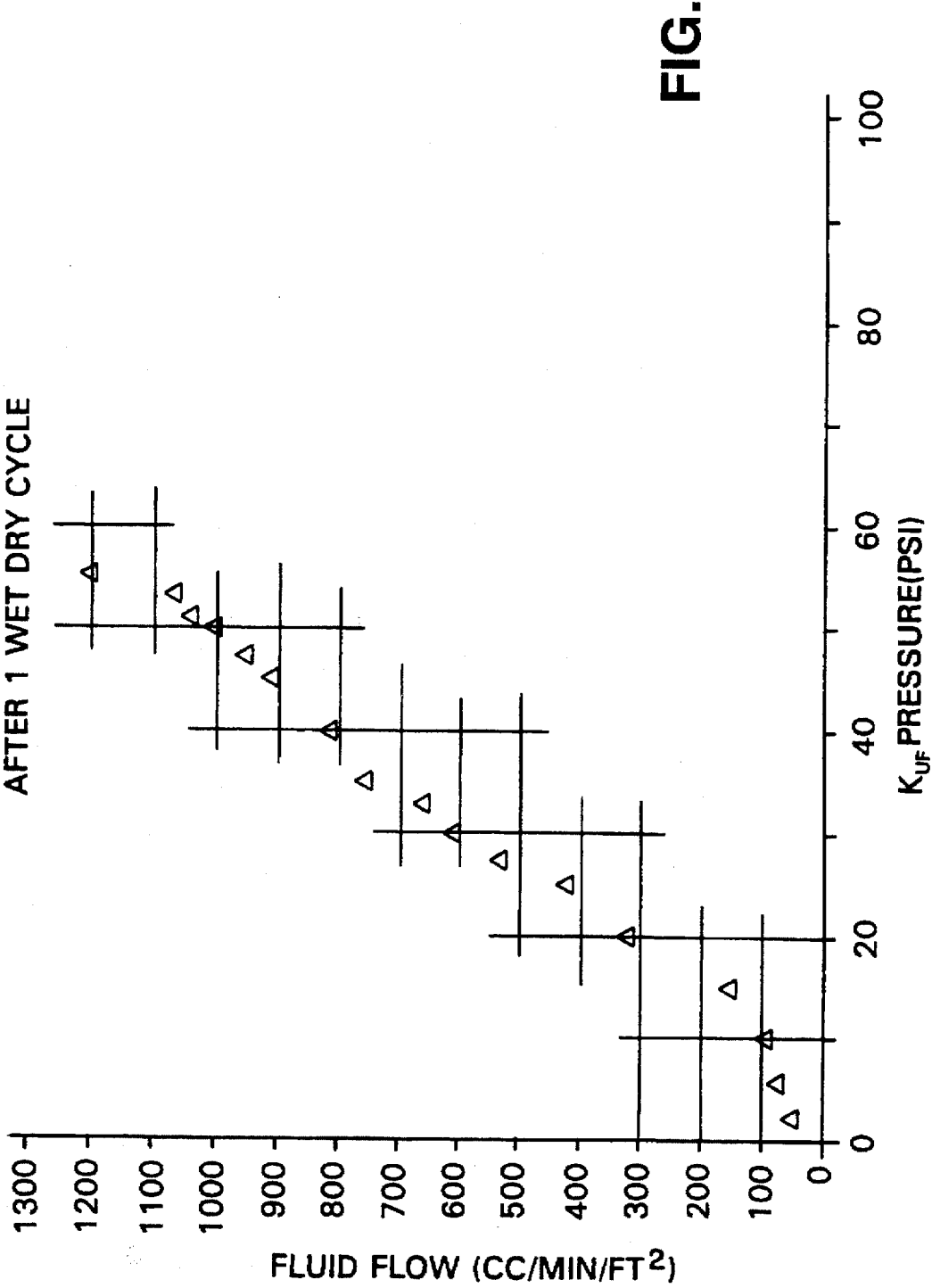
Figure 12:
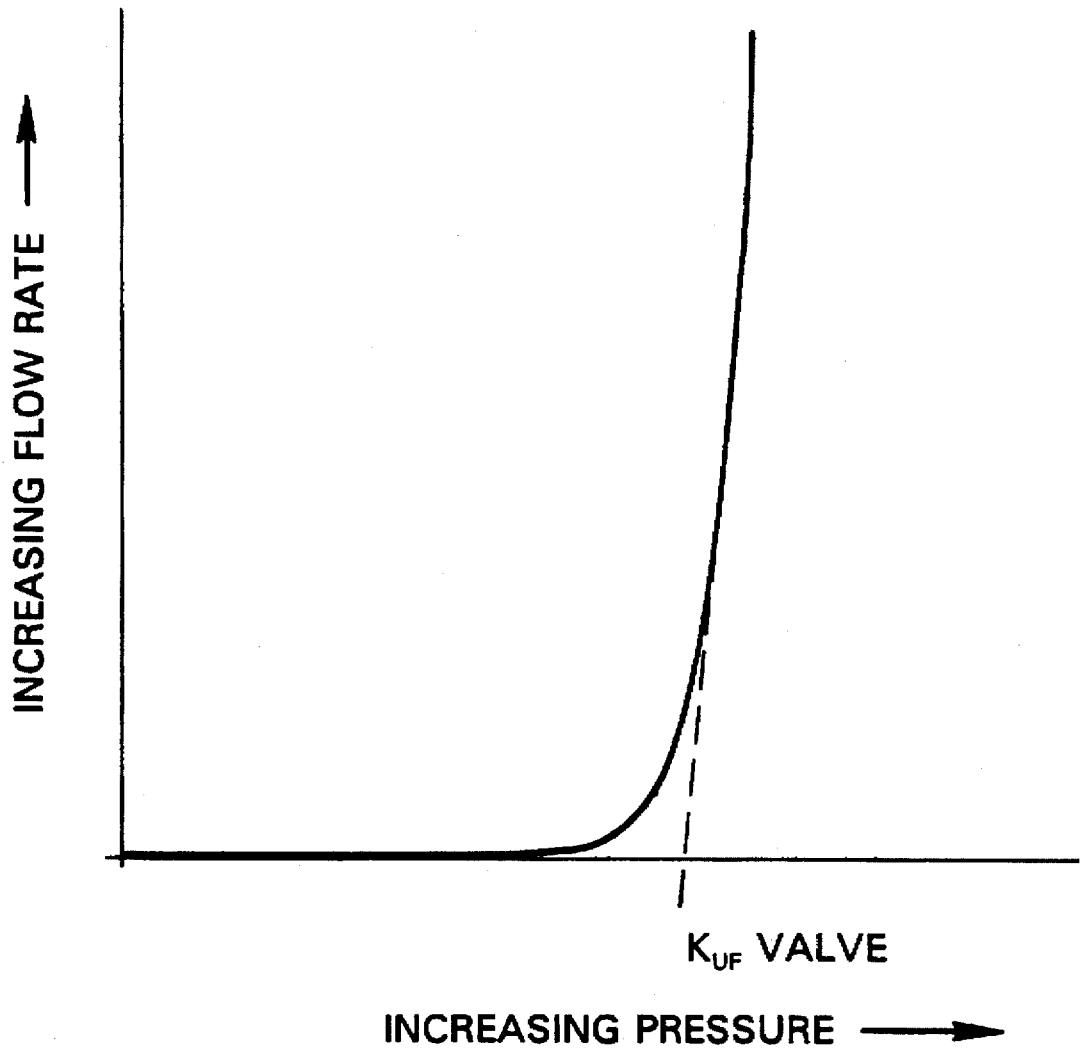
FIG. 12 is a diagram of an idealized $K_{UF}$ curve illustrating the method whereby the $K_{UF}$ value or characteristic pressure is determined.

A $K_{UF}$ curve was obtained on a sample prepared in accordance with the present invention by using the procedure described in Example 11. The sample was wet/dry cycled once using the method of wet/dry cycling described in Example 13. Similarly a Filtron Omega membrane with a rated molecular weight cutoff of 100,000 was $K_{UF}$ tested before and after a single wet/dry cycle. FIGS. 10A–B and FIGS. 11A–B are the resulting $K_{UF}$ curves. A comparison of FIGS. 10A and 10B reveals that the $K_{UF}$ curve for the membrane prepared as per the present invention was essentially unchanged after one wet/dry cycle. In the case of the Filtron Omega membrane, a comparison of FIGS. 11A and 11B. FIG. 11 reveals that after only one wet/dry cycle the shape of the curve has changed. The inflection point, which determines the molecular weight cutoff of the membrane, was shifted to lower pressures. This indicates that after wet/dry cycling the membrane has changed so as to permit larger particles to pass downstream. Continuing to examine the $K_{UF}$ curves of FIG. 11A and 11B, it can be seen that, at test pressures below the inflection point there is a significant flow rate through the membrane even before wet/dry cycling. This is indicative of either defects or large pores which allow fluid flow at low test pressures. The fact that commercially available UF membranes pass significant numbers of monodisperse latex particles much larger than the protein molecules that they are claimed to hold back, is consistent with the $K_{UF}$ curves of FIG. 10A and 10B which indicate that a significant amount of flow occurs at test pressures well below the inflection point in the $K_{UF}$ curve. On the other hand, the membranes described in the present invention have $K_{UF}$ curves that indicate extremely low flow rates at test pressures below the inflection point. An examination of FIG. 10A and 10B reveals that at a $K_{UF}$ test pressure of 10 psi the flow rate through the membrane is almost undetectable when using 1-butanol saturated with water as the wetting fluid and water saturated with 1-butanol as the displacing fluid. The 18K molecular weight cutoff membranes of the present invention are also able to retain 0.02 µm latex particles as demonstrated in Table 4, indicating, that they have sharp molecular weight cutoffs. In contrast, virtually all of the commercially available ultrafiltration membranes failed to retain latex particles with diameters of 0.020 and/or 0.038 µm after they were wet/dry cycled three times and in most cases even if they were not wet/dry cycled.

TABLE 5

| $K_{UF}$ (psi) | $1/K_{UF}$ | Rated molecular Weight Cutoff (Daltons) | Membrane Type |
| --- | --- | --- | --- |
| 9.0 | 0.11 | 300000 | Amicon 300K |
| 23.0 | 0.04 | 100000 | Filtron 100K |
| 40.0 | 0.03 | 50000 | Amicon 50K |
| 50.0 | 0.02 | 30000 | Filtron 30K |
| 71.0 | 0.01 | 10000 | Filtron 10K |

What is claimed is:

1. An ultrafiltration polymeric membrane comprising a skin that is capable of excluding 0.04 µm diameter, monodisperse, latex particles with a rejection coefficient greater than 0.998 after said membrane has been fully dried, and wherein said membrane has a $K_{UF}$ flow rate at 10 psi, using 1-butanol saturated with water as the wetting liquid and water saturated with 1-butanol as the displacing liquid at ambient temperature, below 50 cc/min per square foot of membrane area after being wet/dry cycled at least once.

2. The membrane of claim 1, wherein said membrane is capable of excluding 0.02 µm diameter, monodisperse, latex particles with a rejection coefficient greater than 0.998 after having been fully dried.

3. The membrane of claim 2, wherein said membrane has a pore size rating from 10 angstroms to 200 angstroms.

4. The membrane of claim 2, wherein said membrane is comprised of polysulfone.

5. A process for filtering a fluid comprising causing said fluid to flow through a membrane of claim 4.

6. The membrane of claim 2, wherein said membrane is comprised of polyethersulfone.

7. A process for filtering a fluid comprising causing said fluid to flow through a membrane of claim 6.

8. The membrane of claim 2, wherein said membrane is comprised of polyphenylsulfone.

9. A process for filtering a fluid comprising causing said fluid to flow through a membrane of claim 8.

10. The membrane of claim 2, wherein said membrane is comprised of polyethersulfone blended with from 1 to 50 percent of a compatible polymer.

11. A process for filtering a fluid comprising causing said fluid to flow through a membrane of claim 10.

12. A process for filtering a fluid comprising causing said fluid to flow through a membrane of claim 2.

13. The membrane of claim 1, wherein said membrane has a molecular weight cutoff rating of 100,000 daltons or less.

14. The membrane of claim 13, wherein said membrane has a molecular weight cutoff rating of 20,000 daltons or less.

15. The membrane of claim 1, wherein said membrane has a $K_{UF}$ value of from 5 psi to 120 psi determined using 1-butanol, saturated with water, as the wetting liquid, and water, saturated with 1-butanol, as the displacing liquid.

16. The membrane of claim 15, wherein said membrane has a $K_{UF}$ value of from 10 psi to 120 psi determined using 1-butanol, saturated with water, as the wetting liquid, and water, saturated with 1-butanol, as the displacing liquid.

17. A process for filtering a fluid comprising causing said fluid to flow through a membrane of claim 1.

18. The process of claim 17, wherein said fluid contains proteins and the filtration removes at least some of said proteins from said fluid.

19. The process of claim 17, wherein said fluid contains viruses and the filtration removes at least some of said viruses from said fluid.

20. The process of claim 17, wherein said fluid comprises blood or a blood component.

21. A method for manufacturing an ultrafiltration membrane comprising (a) dissolving a polymeric resin in a carrier comprising both a solvent for the resin and a nonsolvent for the resin to form a solution, wherein the resin is present in an amount from 15 to 20 weight percent of the solution, and the amount of nonsolvent is from 26 to 34 weight percent of the solution, with the ratio of solvent to nonsolvent being from 1.5:1 to 2:1, such that the total amount of resin, solvent, and nonsolvent does not exceed 100%, (b) rapidly mixing the solution to reduce or eliminate the presence of gel particles, (c) filtering the solution to remove any gel particles that are present, (d) degassing the solution to remove any entrained gas, (e) casting or spinning the solution onto a support, and (f) contacting the resulting cast or spun solution with a setting bath that comprises both a solvent and a nonsolvent for the resin.

22. The method of claim 21, wherein said membrane is capable of excluding 0.04 µm diameter, monodisperse, latex particles with a rejection coefficient greater than 0.998 after having been fully dried.

23. The method of claim 22, wherein said membrane has a $K_{UF}$ value of from 5 psi to 120 psi determined using 1-butanol, saturated with water, as the wetting liquid, and water, saturated with 1-butanol, as the displacing liquid.

24. The method of claim 23, wherein said membrane has a $K_{UF}$ value of from 10 psi to 120 psi determined using 1-butanol, saturated with water, as the wetting liquid, and water, saturated with 1-butanol, as the displacing liquid.

25. The method of claim 21, wherein said membrane is capable of excluding 0.02 µm diameter, monodisperse, latex particles with a rejection coefficient greater than 0.998 after having been fully dried.

26. The method of claim 25, wherein said membrane has a pore size rating from 10 angstroms to 200 angstroms.

27. The method of claim 25, wherein said membrane has a $K_{UF}$ flow rate at 10 psi, using 1-butanol saturated with water as the wetting liquid and water saturated with 1-butanol as the displacing liquid at ambient temperature, below 50 cc/min per square foot of membrane area after being wet/dry cycled at least once.

28. The method of claim 25, wherein said membrane is comprised of polysulfone.

29. The method of claim 25, wherein said membrane is comprised of polyethersulfone.

30. The method of claim 25, wherein said membrane is comprised of polyphenylsulfone.

31. The method of claim 25, wherein said membrane is comprised of polyethersulfone blended with from 1 to 50 percent of a compatible polymer.

32. The method of claim 21, wherein said membrane has a molecular weight cutoff rating of 100,000 daltons or less.

33. The method of claim 32, wherein said membrane has a molecular weight cutoff rating of 20,000 daltons or less.

34. A method for manufacturing an ultrafiltration membrane comprising (a) dissolving a polymeric resin in a carrier comprising both a solvent for the resin and a nonsolvent for the resin, wherein the resin is present in an amount from 15 to 20 weight percent, and the amount of nonsolvent is from 26 to 34 weight percent of the solution, with the ratio of solvent to nonsolvent being from 1.5:1 to 2:1, (b) rapidly mixing the solution to reduce or eliminate the presence of gel particles, (c) degassing the solution to remove any entrained gas, (d) casting or spinning the solution onto a support, and (e) contacting the resulting cast or spun solution with a setting bath that comprises both a solvent and a nonsolvent for the resin.

* * * * *